United States Patent [19]
Regan et al.

[11] Patent Number: 5,571,506
[45] Date of Patent: Nov. 5, 1996

[54] AROMATIC OLIGOMERIC COMPOUNDS USEFUL AS MIMICS OF BIOACTIVE MACROMOLECULES

[75] Inventors: John R. Regan, Princeton, N.J.; Daniel G. McGarry, King of Prussia, Pa.; Michael N. Chang, Newtown, Pa.; Jeffrey N. Barton, Philadelphia, Pa.; Jack Newman, Warrington, Pa.; Schmuel Ben-Sasson, Jerusalem, Israel

[73] Assignee: Rhone-Poulenc Rorer Pharmaceuticals Inc., Collegeville, Pa.

[21] Appl. No.: 119,456

[22] Filed: Sep. 10, 1993

Related U.S. Application Data

[63] Continuation of Ser. No. 703,061, May 20, 1991, abandoned, which is a continuation-in-part of Ser. No. 440,584, Nov. 22, 1989, abandoned, Ser. No. 440,586, Nov. 22, 1989, abandoned, and Ser. No. 393,873, Aug. 14, 1989, abandoned.

[51] Int. Cl.$^6$ .............................. A61K 31/775; C08G 8/04
[52] U.S. Cl. ..................... 424/78.17; 424/78.37; 528/139; 528/141; 528/143; 528/148; 528/149; 528/150; 528/151; 514/82; 514/824
[58] Field of Search .............................. 424/484, 78.08, 424/78.26, 78.37; 514/822, 824, 950; 528/148, 129, 181, 204, 206, 218, 210

[56] References Cited

U.S. PATENT DOCUMENTS

| | | | |
|---|---|---|---|
| 2,910,484 | 10/1959 | De Stevens et al. | 528/148 |
| 3,035,973 | 5/1962 | Klotz | 424/456 |
| 4,604,404 | 8/1986 | Munson et al. | 514/494 |
| 4,617,336 | 10/1986 | Pastor et al. | 560/75 |
| 5,324,506 | 6/1994 | Calvo et al. | 424/61 |

FOREIGN PATENT DOCUMENTS 9103226  3/1991  WIPO.

OTHER PUBLICATIONS

Schenk, et al., J. Am. Chem. Soc. 1991, (113), 2634–2647 1991; "Novel Oligo(phenylenevinylenes): Models for the Charging of Extended π chains".
Plastic Materials, J. A. Brydson, Newings–Butterworths, London 1975, pp. 474–476, 514–515.
Gutsche, Top. Curr. Chem. 123 1–47, (1984); "The Calixarenes".
Bohmer, et al., J. Org. Chem. 1987, (52), 3200–3205, 1987; "Calix[4]arenes with Four Differently Substituted Phenolic Units".
Royer, et al., Tetrahedron Letters, vol. 28, No. 52, pp. 6595–6596, 1987, "Synthesis of Calix[4]arenes Presenting No Plane of Symmetry".
Hakimelahi, et al., Helvetica Chimica Acta, vol. 64, Fasc. 2, 1981–Nr.59, "The Synthesis of Polyfunctional Aromatic Ring Systems. Structural Analogues of Phloroglucides, Aranciamycin, Cryptosporin and Terramycin" pp. 599–609.
Gutsche, et al., J. Org. Chem. 1982, (42), 2708–2712, 1982 "Calixarenes, 7, p–Phenylcalix[4]arene ".
Gutsche, Acc. Chem. Res. 1983, (16), 161–170, 1983 "Calixarenes".
Chawla, et al., Bull. Soc. Chim. Fr. 1991 (Mar.–Apr.) 232–243, 1991, "Hydrolysis of Phenyl Benzoates in the Presence of p–tert–butyl–, p–octyl– and p–methyl Calix[n]arenes".
Kammerer, et al., Monatshefte fur Chemie (109) 767–773 1978, "Die stufenweise Synthese von4,11,18,25–Tetra–tert–butyl[1.1.1.1]metacyclophan7,14,21,28–tetraol und 4,11–Dimethyl[1.1.1.1]metacyclophan–7,14,21,28–tetraol".
Kammerer, et al., Monatshefte fur Chemie (112)759–768 1981 "Die stufenweise Synthese o,o'–methylenverbruckter Cyclohexamerer mit p–Kresol– oder p–Kresol–und 4–tert–Butylphenol–Bausteinen Vergleich mit ahnlich strukturierten Kettenoligomeren".
Kammerer, et al., Makromol. Chem. (179),1199–1207 1978 "Stufenweise Darstellung von Cyclo[quater [(5–alkyl–2–hydroxy–1,3–phenylen)methylen]]en und ihr Vergleich mit linearen phenolischen Mehrkernverbindungen".
Kammerer, et al., Makromol. Chem. (181), 2049–2062 1980 "Stufenweise Darstellung eines Cycloheptamers aus p–Kresol, 4–tert–Butylphenol und Formaldehyd. Vergleich mit einem phenolischen, heptanuklearen Kettenoligomer".
Kammerer, et al., Makromol. Chem. (182), 1685–1694 1981 Schrittweise Synthesen und Eigenschaften einiger Cyclopentamerer aus methylenverbruckten (5–alkyl–2–hydroxy–1,3–phenylen)–Bausteinen.
Bohmer, et al., Makromol. Chem. (182) 2671–2686 1981 "Darstellung von Oligo[(hydroxy–1,3–phenylen)methylen] en mit Hydroxynitrophenylen–und Alkylhydroxyphenyleneinheiten".
Hayes, et al., J. appl. Chem., (8) Nov., 1958 "Phenol–Formaldehyde and Allied Resins VI: Rational Synthesis of a 'Cyclic' Tetranuclear p–Cresol Novolak" pp. 743–748.
Arduini, et al., Tetrahedron vol. 46, No. 10, pp.3613–3620, 1990 "Synthesis and Structural Characterization of Regio–Controlled Oligomers from 2–Naphthalensulfonic Acid and Formaldehyde".
No, et al., J.Org.Chem. 1982(47), 2713–2719 "Calixarenes.8. Short, Stepwise Synthesis of p–Phenylcalix(4)arene, p–phenyl p–tert–butylcalix(4)arene,and Derived Products".
The Merck Index, Editor, Martha Windholz, p. 312, entry 2182.

*Primary Examiner*—Edward J. Webman
*Attorney, Agent, or Firm*—Paul R. Darkes; Martin F. Savitzky

[57] ABSTRACT

This invention relates to aromatic oligomeric compounds useful in the treatment of cardiovascular, bone metabolic, hypolipidaemic, neuronal, gastrointestinal and elastase-mediated connective tissue degradation disorders and disorders which may be treated by agents effective in binding DNA, to processes for preparation of such oligomeric compounds, to pharmaceutical compositions including such oligomeric compounds, and to their use in the treatment of such disorders.

32 Claims, No Drawings

AROMATIC OLIGOMERIC COMPOUNDS USEFUL AS MIMICS OF BIOACTIVE MACROMOLECULES

CROSS-REFERENCE TO RELATED APPLICATIONS

This is a continuation of application Ser. No. 07/703,061 filed on May 20, 1992, now abandoned, which is a continuation-in-part of U.S. applications Ser. Nos. 07/440,584 and 07/440,586, both filed Nov. 22, 1989, both abandoned and U.S. application Ser. No. 07/393,873, filed Aug. 14, 1989, now abandoned.

The inventions described in the aforementioned applications describe and claim pharmaceutical compositions containing a class of aromatic polymeric compounds and the use of such compositions in pharmaceutical applications. The present application is concerned with a novel class of aromatic oligomers and with their use in pharmaceutical applications, including applications of the type referred to in the aforementioned applications.

FIELD OF THE INVENTION

The present invention relates to: (A) methods of treatment involving the use of pharmaceutical compositions containing aromatic oligomers which mimic the action of bioactive naturally ocurring polymers including glycosaminoglycans, peptides and polynucleic acids; (B) pharmaceutical compositions containing such oligomers; and (C) novel oligomers for use in such compositions and treatments.

Glycosaminoglycans (GAG) are linear polysaccharides formed by characteristic repeating disaccharide units usually composed of a uronic acid and a hexosamine. The term "acid mucopolysaccharides" was used originally to designate hexosamine-rich acid polysaccharides extracted from connective tissue. In recent years, the term "glycosaminoglycans" has gained greater acceptance and is now used in place of mucopolysaccharides. The hexosamine can be glucosamine or galactosamine, and the uronic acid can be glucuronic or iduronic acid. Sulphate groups are found on all glycosaminoglycans apart from hyaluronic acid, and all of the sulphated glycosaminoglycans are covalently linked to protein forming different classes of proteoglycans. However, it would be an oversimplification to consider glycosaminoglycans to be simple repeat-unit polysaccharides, since considerable chemical and configurational variability can be superimposed upon the component sugars.

Among other functions it has been shown that the glycosaminoglycans serve as a support which binds various bioactive peptides. This association is based on a non-covalent interaction since the bound protein can be readily released upon the addition of free glycosaminoglycans. Well known examples of such bound proteins include enzymes such as lipoprotein lipase (LPL) or growth-regulating peptides such as fibroblast growth factor (FGF). Another example of GAG-protein interaction is that of the enzyme heparinase which participates in cell-invasion processes. It has been demonstrated also that the commercially available glycosaminoglycan, heparin, inhibits the growth of vascular smooth muscle cells and the proliferation of kidney mesangial cells. The former cell type is involved in arteriosclerosis while the latter plays a role in glomerulosclerosis.

Heparin is known also to be involved in the release of lipoprotein lipase, the inhibition of heparinase and the release of fibroblast growth factor. The most common application of heparin is as an anticoagulant where heparin interacts with proteins which play a key role in hemostasis.

Glycosaminoglycans such as heparin are a major constituent participating in the composition of various biological structures such as basement membranes, connective tissues, cartilage and cell-surface glycocalyx. Connective tissues are responsible for providing and maintaining form in the body. Functioning in a mechanical role, they provide a matrix that serves to connect and bind the cells and organs and ultimately give support to the body. Unlike the other tissue types (epithelium, muscle and nerve) formed mainly by cells, the major constituent of connective tissue is its extracellular matrix, composed of protein fibers, an amorphous ground substance, and tissue fluid, the latter consisting primarily of bound water of solvation. Embedded within the extracellular matrix are the connective tissue cells.

In terms of structural composition, connective tissue can be subdivided into three classes of components: cells, fibers and ground substance. The wide variety of connective tissue types in the body represents modulations in the degree of expression of these three components.

The amorphous intercellular ground substance fills the space between cells and fibers of the connective tissue; it is viscous and acts as a lubricant and also as a barrier to the penetration of the tissues by foreign particles. Glycosaminoglycans and structural glycoproteins are the two principal classes of components comprising the ground substance.

Various disease states are characterized by the pathological hydrolysis of structural glycoproteins such as collagen, fibronectin and elastin. This hydrolysis can be mediated by the enzyme, elastase, which is possibly the most destructive enzyme in the body. The elastase produced by human neutrophil leukocytes (otherwise known as PMN or HNE or HLE) is believed to be involved in various diseases characterized by the destruction of structural proteins comprising the ground substance, including pulmonary emphysema, chronic bronchitis, cystic fibrosis, bronchiectasis, adult respiratory distress syndrome, atherosclerosis, arthritis, psoriasis, vasculitis, glomerulonephritis and consumption coagulopathies associated with gram-negative sepsis or leukemias.

The present invention is based on the discovery of a class of compounds exhibiting properties which mimic the action of glycosaminoglycans and which are capable of modulating biological systems containing complexes between bioactive peptides and/or proteins and glycosaminoglycans by competing with the binding interactions of glycosaminoglycans.

REPORTED DEVELOPMENTS

Heparin has been used for decades as an anticoagulant in situations where intravenous administration thereof can be monitored and controlled. More recently, purified fractions of heparin have been used as a more effective substitute. Nevertheless, both complete or fractionated heparin require intravenous administration.

The aforementioned applications Ser. Nos. 07/393,873, 07/440,584, and 07/440,586, hereby incorporated by reference, disclose pharmaceutical compositions comprising, in admixture with a pharmaceutically acceptable carrier, therapeutically effective amounts of aromatic ring-containing polymeric compounds, substantially free of monomer, and having properties which mimic the pharmacological activity of glycosaminoglycans and which are capable of competing with the binding thereof to bioactive peptides and/or proteins. Examples of such polymeric compounds include those having a molecular weight of about 2,000 to about 20,000

Daltons and in which each monomeric unit of the polyaromatic compound includes from 1 to about 10 aromatic rings, which may be substituted by electronegative substituents and/or negatively charged residues.

In the earliest '873 application, the preferred compounds for use in the pharmaceutical compositions are disclosed to be those in which each monomeric unit contains between 3 and 10 aromatic rings, and particularly those in which the aromatic rings contain at least one substituent on at least two of the rings. The preferred molecular weight of these polymeric compounds are described as being about 2000 to about 20,000, the most preferred molecular weight being about 2000 to about 4000 Daltons, as measured by gel permeation chromatography. Another aspect of the invention described and claimed in the aforementioned '873 application includes use of the aforementioned pharmaceutical compositions to treat humans or other animals for cardiovascular disorders, metabolic disorders of bone tissue, and neuronal disorders.

Aromatic polymers described in the aforementioned '873 application exhibit anticoagulant properties, are capable of being administered orally and are capable of being absorbed into the bloodstream from the gastrointestinal tract.

In application Ser. No. 07/440,854, there is disclosed a biologically active polymeric compound having an alkylaryl backbone, including particularly those polymeric compounds which have about 5 to about 50 repeating monomeric or dimeric aromatic ring-containing units. More specifically, there is disclosed a biologically active polymeric compound having an alkylaryl backbone and from about 5 to about 50 repeating monomeric or dimeric aromatic ring-containing units and which, according to the computer program marketed as SYBYL version 5.2 running on a DEC VAX 11/750 computer, is capable of forming a linear backbone having a helical secondary structure, and wherein the maximum diameter of the helical structure, as measured by the alkylaryl backbone, is less than 3 times greater than the maximum diameter of the aryl group of the alkylaryl backbone. In preferred form, the polymeric compound is substantially linear and includes polymeric compounds in which the alkylaryl group is polysubstituted.

Application Ser. Nos. 07/440,854 and 07/440,856, disclose a class of polymeric compound including as a repeating unit in the polymeric chain a single mononuclear aromatic ring or a single polynuclear aromatic ring. which are prepared by polymerizing a monomeric form of a compound which comprises a mononuclear aromatic ring, for example, phenylenes such as hydroxybenzoic acid, or by polymerizing a monomeric form of a compound which comprises a polynuclear aromatic ring, for example, naphthalenes such as hydroxynaphthoic acid. Another class of polymeric compounds of the aforementioned type, that is, those which have the computer-predicted helical secondary structure as referred to above, comprise polymeric compounds which include as a repeating unit in the polymeric chain two substituted aromatic ring-containing units, each of the aromatic ring-containing units being substituted with the same group(s) and being bonded together by an alkyl bridge. Preferably, the positions of the corresponding substituents of each ring have the same orientation (for example, ortho-, meta- or para-) with regard to the position of the alkyl bridge. The most preferred compounds are those which comprise as the repeating unit in the polymeric chain two identically-substituted phenylene groups and wherein the alkyl bridging groups are attached to each phenylene in an orientation meta- to each other. Such polymeric compounds can be prepared by forming first the dimer of the monomeric form of the compound comprising the aromatic ring and then polymerizing the dimer.

Although considerable efforts have been directed to the isolation, from the aforesaid polymeric reaction mixtures, of a narrow band molecular weight fraction of the resulting polymeric material, the fractionated materials obtained nevertheless comprise mixtures of more than one polymeric species differing primarily in the number of monomeric units making up each polymeric component of the fractionated mixture. That the polymeric product is a mixture is of concern in connection with various governmental health authority requirements regulating the approval for commercial use of pharmaceutical products. Such requirements mandate the precise reproducibility of the process used to produce the drug submitted for approval. Since the mixture of bioactive aromatic polymers discussed hereinabove is produced from a polymerization reaction, the reproducibility of the product obtained from the polymeric mixture and subsequent fractionation, in terms of all chemical physical and biological properties, would be expected to come under intense governmental scrutiny. Consequently, continuing work has focused on the precise manufacture of the bioactive aromatic polymer, and, in particular, has focused on a process for the preparation of oligomeric compounds, that is compounds having a precisely defined molecular weight and monomer number content yet retaining the chemical, physical and biological characteristics of the polymeric materials described hereinabove.

The literature discloses oligomeric compounds characterized by extended $\pi$ chains, such as disclosed in Schenck, et al., *J. Am. Chem. Soc.* 113 (7), 2634–2647 (1991), oligo(phenylene-vinylenes), and oligo(hydroxyphenylmethylenes) utilized as intermediates for the preparation of calixarenes, which are cyclic oligomers comprising $[1_n]$ metacyclophanes made up of para-substituted phenolic units and methylene groups such as disclosed, for example, in Gutsche, *Top. Curr. Chem.* 123, 1–47 (1984); Bohmer, et al., *J. Org. Chem.* 52 (15) 3200–3205 (1987); Royer, et al., *Tetrahedron Lett.* 28 (52), 6595–6596 (1987). The aforesaid Gutsche reference discloses that certain of the calixarenes as well as linear tetramers made up of p-halophenol units exhibit activity against various pathogenic organisms. Similarly, smaller oligomer compounds, such as the trimer, 3,5-bis-(2,4-dihydroxy-6-methoxy-5 -methyl-3-propanoyl-benzyl)-2,4,6-trihydroxybutyrophenone (i.e. trisaspidinol), synthesized as an analogue of terramycin, has been reported to possess antibacterial activity, Hakimelahi, et al., *Helv. Chim. Acta* Vol. 64, Fasc. 2, 599–609 (1981).

SUMMARY OF THE INVENTION

As is described in more detail below the present invention relates to pharmaceutical compositions comprising, in admixture with a pharmaceutically acceptable carrier, aromatic oligomeric compounds, comprising a single molecular species having an ascertainable molecular weight and between 4 to about 50 linked structural units, and capable of mimicking the action of bioactive naturally ocurring polymers including glycosaminoglycans, peptides and polynucleic acids.

The present invention relates specifically to pharmaceutical compositions comprising, in admixture with a pharmaceutically acceptable carrier, an oligomeric compound according to Formula I $$M_t\text{-}(M_n)_n\text{-}M_t \qquad \text{I}$$

wherein:
  n represents a sequence of whole numbers beginning at 2 and and terminating at less than or equal to about 50;
  $M_i$ is

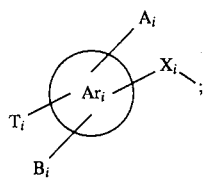

$M_n$ is

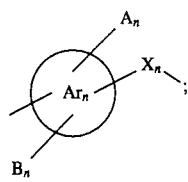

$M_t$ is

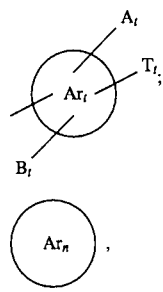

$A_n$, $B_n$, and $X_n$ may be the same or different for each of the $(M_n)_n$ groups in the n sequence;

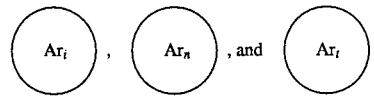

are independently aromatic carbocyclic or aromatic heterocyclic rings,
  $A_i$, $B_i$, $A_n$, $B_n$, $A_t$, $B_t$, $T_i$ and $T_t$ are independently hydrogen or a substituent group;
  $X_i$, and $X_n$ are independently a bond, alkylene, unsaturated alkylene, or heteroatom-containing linking group;
or a pharmaceutically acceptable salt thereof.

A further aspect of the present invention relates to oligomeric compounds having at least one substituent group or pro-substituent group capable of participating in electrostatic interactions with bioactive molecules at biological pH according to Formula I above, and wherein n represents a sequence of whole numbers beginning at 3 and and terminating at less than or equal to about 50.

Still another aspect of the present invention relates to pharmacological methods comprising the administration of an effective amount of said pharmaceutical composition to a human or other animal patients in need of cardiovascular therapy such as anticoagulant and/or antithrombotic therapy and/or bone metabolic therapy and/or antihypolipaemia therapy and/or therapy for the treatment of neuronal disorders and/or gastrointestinal disorders and/or disorders which may be treated by agents effective in binding DNA.

Underlying a further aspect of the present invention is the surprising and unexpected discovery that a preferred class of oligomers according to the present invention are characterized as highly selective and potent inhibitors of the enzyme, elastase, which is produced by human polymorphonuclear neutrophils (PMN). Accordingly, another aspect of the present invention relates to pharmacological methods comprising the administration of a pharmaceutical composition comprising an effective elastase-inhibiting amount of a said oligomer to a human or other animal patient suffering from an elastase-mediated connective tissue degradation disorder.

Some advantages which flow from the practice of the present invention include extended duration of bioactivity in-vivo, as compared to naturally occurring compounds such as heparin, and the availability of oral administration. Heparin, for example, cannot be administered orally, as it is degraded in the digestive system before being absorbed into the bloodstream. In practice, however, it is anticipated that for many therapies the preferred mode of administration of the compositions and compounds of the present invention will be parenteral, for example, intravenous injection.

DETAILED DESCRIPTION OF THE INVENTION

As used above, and throughout the description of this invention, the following terms, unless otherwise indicated, shall be understood to have the following meanings:

"Aromatic carbocyclic ring" means an aromatic hydrocarbon ring system. Preferred aromatic carbocyclic rings include benzene and naphthalene.

"Aromatic heterocyclic ring" means about a 5- to about a 15- membered monocyclic or multicyclic aromatic ring system in which one or more of the atoms in the ring or rings is an element other than carbon, for example nitrogen, oxygen or sulfur. Preferred aromatic heterocyclic rings include pyridine, quinoline, and isoquinoline.

"Alkyl" means a saturated aliphatic hydrocarbon group which may be straight or branched and having about 1 to about 20 carbon atoms in the chain. Branched means that a lower alkyl group such as methyl, ethyl or propyl is attached to a linear alkyl chain. Preferred alkyl groups are the "lower alkyl" groups which are those alkyl groups having from 1 to about 6 carbons.

"Aryl" means phenyl or naphthyl, or phenyl or naphthyl substituted with one or more aryl group substituents which may be the same or different, where "aryl group substituent" includes alkyl, alkenyl, alkynyl, aryl, aralkyl, hydroxy, alkoxy, aryloxy, aralkoxy, hydroxyalkyl, acyl, formyl, carboxy, alkenoyl, aroyl, halo, nitro, trihalomethyl, cyano, alkoxycarbonyl, aryloxycarbonyl, aralkoxycarbonyl, amino, alkylamino, and dialkylamino.

"Aralkyl" means an alkyl group substituted by an aryl radical. Exemplary aralkyl groups include benzyl and phenethyl.

"Halogen (halo)" means fluorine (fluoro), chlorine (chloro), bromine (bromo) or iodine (iodo).

"Alkenyl" means an alkyl group containing a carbon—carbon double bond. Exemplary groups include allyl and vinyl.

"Alkoxy" means an alkyl-O— group. Lower alkoxy groups are preferred. Exemplary groups include methoxy, ethoxy, n-propoxy, i-propoxy and n-butoxy.

"Aralkoxy" means an aralkyl-O— group. Exemplary groups include benzyloxy and phenethyloxy.

"Aryloxy" means an aryl-O— group. Exemplary groups include phenoxy and 2-naphthyloxy.

"Acyl" means an

group. Preferred acyl groups are those in which the alkyl group is lower alkyl.

"Alkoxycarbonyl" means an

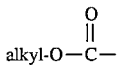

group. Preferred groups include methoxycarbonyl and ethoxycarbonyl.

"Aralkoxycarbonyl" means an

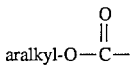

group. A preferred group is benzyloxycarbonyl.

"Aryloxycarbonyl" means an

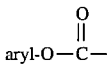

group. A preferred group is phenoxycarbonyl.

"Biological pH" refers to that pH of blood, plasma or serum in the body between about 7.2 and about 7.5 and which does not interfere with normal degradation of materials present therein. The normal pH of blood, plasma or serum values is about 7.35–7.45 and is preferably about pH 7.39–7.41.

The oligomers of the present invention are described by Formula I wherein the number of individual units making up the oligomer are provided for by the use of sequence notation. More particularly, the formula is dependent on the variable "n" which is defined in the Summary of Invention section hereinabove as a sequence of whole numbers beginning at 2 and having an upper limit of about 50. For n=2, the oligomer according to Formula I is a tetramer of the formula $M_i$-$M_1$-$M_2$-$M_t$; for n=4, the oligomer is a hexamer of the formula $M_i$-$M_1$-$M_2$-$M_3$-$M_4$-$M_t$; and for n=6, the oligomer is an octomer of the formula $M_i$-$M_1$-$M_2$-$M_3$-$M_4$-$M_5$-$M_6$-$M_t$. The variable "n" serves to identify not only the individual oligomeric units in the sequence of units making up the oligomer, but also serves to differentiate the various $Ar_n$ units with their associated substituent and linking groups, $A_n$, $B_n$, and $X_n$. For example, $M_4$ is equivalent to the group $Ar_4$ with substituent groups, $A_4$ and $B_4$, and linking group $X_4$.

This means of defining the oligomers according to the present invention highlights the variability in oligomer sequence order and chemical makeup that is enabled by the oligomer preparation processes disclosed herein. By virtue of the processes disclosed herein, the preparation of oligomers characterized by specific molecular weight, differing oligomeric unit content and specific oligomeric unit sequence, specifically chosen and located linking groups is possible. This ability to design a discrete oligomeric molecule of specific chain length and characterized by a selected functionalization and/or elimination of substituent groups on specific oligomeric units enables the fine tuning and focusing of the potency, pharmacological specificity and oral bioavailability of the oligomers of the present invention. Consequently, a further aspect of this invention relates to processes for the preparation of the oligomers of the present invention. The particular pharmacological properties and the assays used to determine the pharmacological profiles of the present oligomers is discussed in more detail below.

The preferred oligomeric compounds useful in the pharmaceutical compositions are according to Formula I wherein the substituent and linking groups are defined as follows:

$A_i$, $B_i$, $A_n$, $B_n$, $A_t$, and $B_t$ are independently hydrogen, alkyl, aralkyl, cyano, alkoxyalkoxy, or —(CH$_2$)$_a$—W—(CH$_2$)$_b$—R$_s$, where R$_s$ is NRR', COOR, CONRR', NR(COR'), PO(OR)$_2$, COR, SO$_2$OR, OSO$_2$OR, halogen, OR, SO$_2$R, SOR, SR, or CHO, and where a and b are independently 0 to about 4, (a+b) is less than about 5, W is —O—, —S—, —SO—, —SO$_2$—, —NR(COR')—, —NR—, or a bond, and R and R' are independently hydrogen, alkyl or aralkyl, $T_i$ and $T_t$ are independently hydrogen, alkyl, alkenyl, halo, cyano, alkoxyalkoxy, haloalkyl, hydroxy, tert-butyldimethylsilyloxyalkyl, hydroxyalkyl, alkoxy, aralkoxy, aryloxy, alkoxyalkyl, aralkoxyalkyl, aryloxyalkyl, mercapto, mercaptoalkyl, alkylthio, aralkylthio, alkylthioalkyl, aralkylthioalkyl, arylthioalkyl, amino, alkylamino, aminoalkyl, alkylaminoalkyl, acylamino, acylaminoalkyl, carboxy, carboxyalkyl, alkoxycarbonyl, alkoxycarbonylalkyl, aralkoxycarbonyl, aralkoxycarbonylalkyl, aryloxycarbonyloxy, formyl, formylalkyl, acyl, acyloxy, and acylalkyl, $X_i$ and $X_n$ are independently —(CR$_1$R$_2$)$_m$—Y—(CR$_3$R$_4$)$_p$— where R$_1$, R$_2$, R$_3$, and R$_4$ are independently hydrogen or alkyl, m and p are independently 0 to about 5, provided that (m+p) is 0 to about 5, and Y is a bond, —O—, —S—, cis or trans —CR$_6$=CR$_7$—, —CR$_6$=CR$_7$—CR$_8$=CHR$_9$— where each of the double bonds may independently be cis or trans, —N(R$_5$)—, —N(R$_5$)CO—, —CONR$_5$—, carbonyl, carbonyloxy, or oxycarbonyl where R$_5$, R$_6$, R$_7$, R$_8$ and R$_9$ are independently hydrogen or alkyl.

A more particularly preferred class of compounds useful for the present invention is described by Formula I wherein:

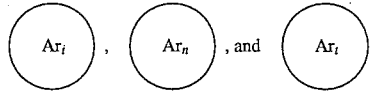

are independently benzene, naphthalene, pyridine, quinoline, or isoquinoline.

Another preferred class of compounds within the scope of the present invention is described by Formula I wherein:

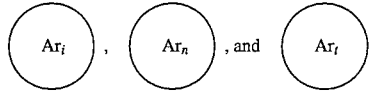

are independently benzene or naphthalene.

A more preferred class of compounds is described by Formula I wherein:

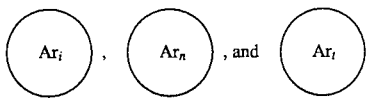

are independently benzene or naphthalene and wherein n is a sequence of whole numbers having an upper limit of from about four to about 8.

Another more preferred class of compounds is described by Formula I wherein:

$M_i$ is

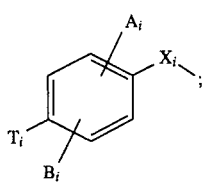

$M_n$ is

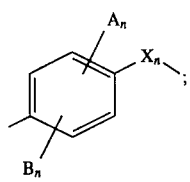

and
$M_t$ is

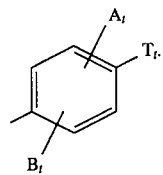

Another more preferred class of compounds is described by Formula I wherein:

$M_i$ is

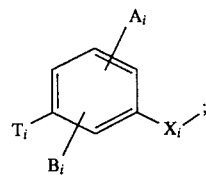

$M_n$ is

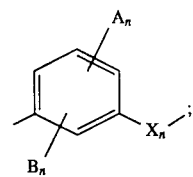

and $M_t$ is

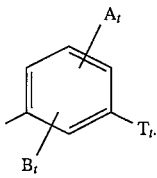

A most preferred class of compounds is described by Formula I wherein:

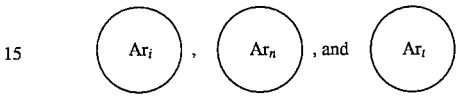

are independently benzene or naphthalene and wherein n is a sequence of whole numbers beginning at 2 and having an upper limit of 18 and wherein $(M_n)_n$ represents from two to about 18 monomeric units.

Another most preferred class of compounds of the present invention is described by Formula I wherein:

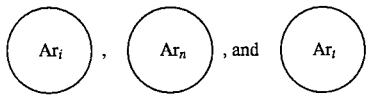

are independently benzene or naphthalene and wherein n is a sequence of whole numbers beginning at 4 and having an upper limit of 14 and wherein $(M_n)_n$ represents from 4 to about 14 monomeric units.

Another most preferred class of compounds of the present invention is described by Formula I wherein:

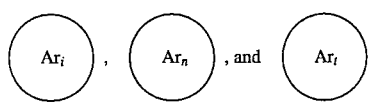

and are independently benzene or naphthalene and wherein n is a sequence of whole numbers beginning at 6 and having an upper limit of 18 and wherein $(M_n)_n$ represents from 6 to about 18 monomeric units.

The compound aspect of the present invention as defined above comprises oligomers having substituent groups (or pro-substituent groups thereof) capable of interacting electrostatically with bioactive molecules such as proteins. For the purposes of this invention, it is understood that substituent groups capable of electrostatic interaction include but are not limited to amines, carboxyl, phosphate, phosphate ester, sulfate, sulfonate, sulfate esters, sulfonate esters, and thiol. It is further understood that the present oligomers can be formulated more conveniently for pharmaceutical administration in a masked or prodrug form utilizing pro-substituent groups which are capable of being metabolized in the body to groups capable of electrostatic interaction. Exemplary groups include but are not limited to amides, esters, alkylcarbonyl, aldehyde and alkyl thiol.

A special embodiment of the present invention is described by Formula II below.

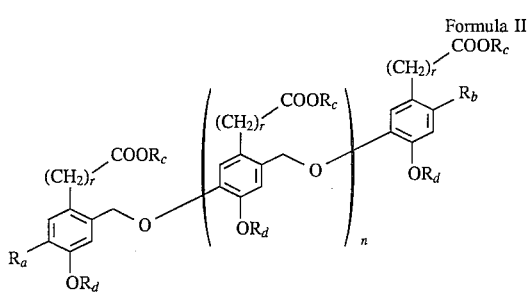

wherein:
$R_a$ is hydrogen, hydroxy, or acyloxy;
$R_b$ is hydrogen, alkyl, or hydroxyalkyl;
$R_c$ is hydrogen or alkyl;
$R_d$ is alkyl or hydrogen;
r is 1 through about 4; and
n is 2 to about 30;
or a pharmaceutically acceptable salt thereof.

Another special embodiment of the present invention is described by Formula III below.

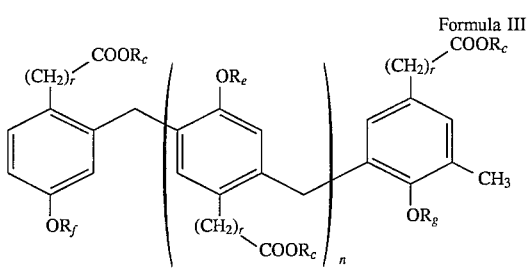

wherein:
$R_e$, $R_f$, and $R_g$ are independently hydrogen or alkyl; and
n is 1 to about 30;
or a pharmaceutically acceptable salt thereof.

Another special embodiment of the present invention is described by Formula I wherein:
$M_i$ is

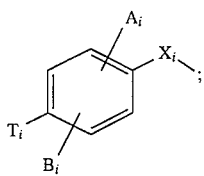

$M_n$ is

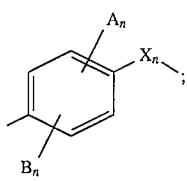

and $M_t$ is

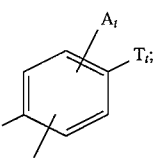

or wherein
$M_i$ is

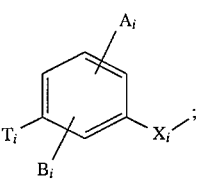

$M_n$

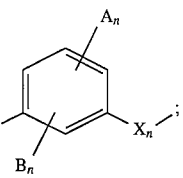

and
$M_t$ is

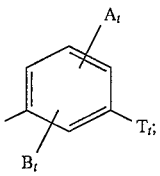

or is described by Formula II or Formula III wherein n is a sequence of whole numbers having an upper limit of from about four to about 8.

Representative compounds of the present invention include:
2-[4-[4-[4-[[5-(2-carboxyethyl)-2-methoxy]phenoxymethyl]-[5-(2 -carboxyethyl)-2-methoxy]phenoxymethyl]-[5-(2-carboxyethyl)-2-methoxy]phenoxymethyl]-[5-(2-carboxyethyl)-2-methoxy]phenoxymethyl]-4 methoxyhydrocinnamic acid

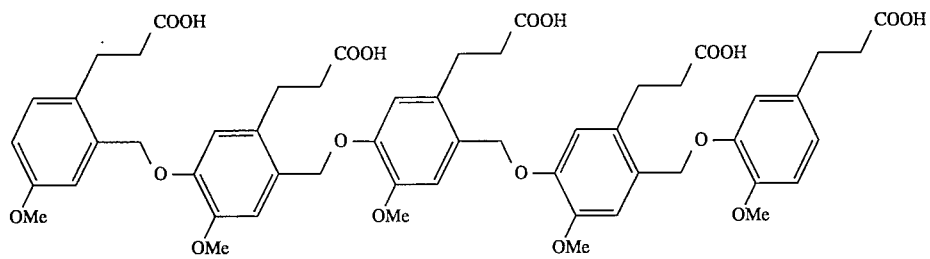

1,2-bis-[4-[4-[4-[[2-(2-carboxyethyl)-5-hydroxy]benzyl]-[2-(2′-carboxyethyl)-5-hydroxy]benzyl]-[2-(2-carboxyethyl)-5-hydroxy]benzyl]-[2-(2′-carboxyethyl)-5-hydroxy]phenyl]ethane

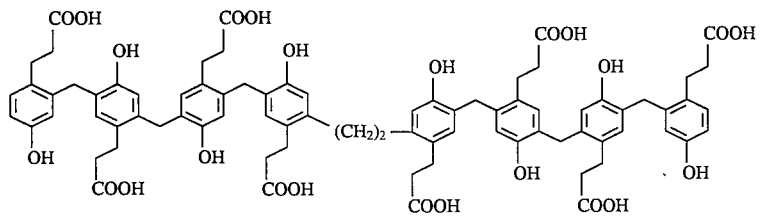

bis-[5-(2-carboxyethyl)-3-[5-(2-carboxyethyl)-2-hydroxybenzyl]-2′-hydroxyphenyl]methane

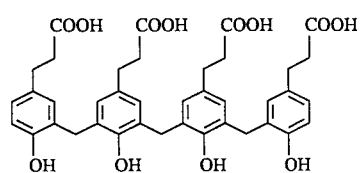

methyl-5-acetoxy-2-[4-[4-[[5-(2-methoxycarbonylethyl)-4-hydroxymethyl-2-methoxy]phenoxymethyl]-[5-(2-methoxycarbonylethyl)-2′-methoxy]phenoxymethyl]-[5-(2-methoxycarbonylethyl)-2′-methoxy]phenoxymethyl]-4-methoxyhydrocinnamate

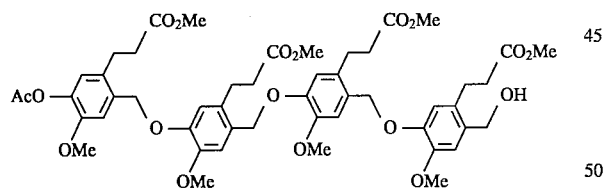

1,2-bis-[2-(2-carboxyethyl)-4-[2-(2-carboxyethyl)-5-hydroxybenzyl]-5′-hydroxyphenyl]ethane

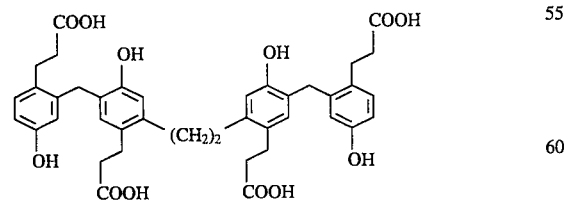

1,2-bis-[4-[4-[4-[[2-(2-carboxyethyl)-5-hydroxy]benzyl]-[2-(2′-carboxyethyl)-5-methoxy]benzyl]-[2-(2-carboxyethyl)-5-methoxy]benzyl]-[2-(2′-carboxyethyl)-5-methoxy]phenyl]ethane

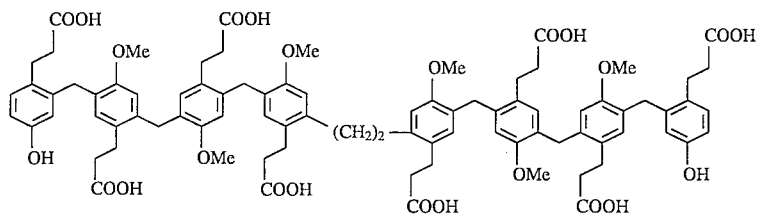

5-[4-[4-[4-[4-[4-[[2-(2-carboxyethyl)-5-hydroxy]benzyl]-[2-(2-carboxyethyl)-5-hydroxy]benzyl]-[2-(2-carboxyethyl)-5-hydroxy]benzyl]-[2-(2-carboxyethyl)-5-hydroxy]benzyl]-[2-(2-carboxyethyl)-5-hydroxy]benzyl]-[2-(2-carboxyethyl)-5-hydroxy]benzyl]-[2-(2-carboxyethyl)-5-hydroxy]benzyl]-4-hydroxy-2-methylhydrocinnamic acid 5-[4-[4-[4-[4-[4-[[2-(2-carboxyethyl)-5-hydroxy]benzyl]-[2-(2-carboxyethyl)-5-methoxy]benzyl]-[2-(2-carboxyethyl)-5-methoxy]benzyl]-[2-(2-carboxyethyl)-5-methoxy]benzyl]-[2-(2-carboxyethyl)-5-methoxy]benzyl]-[2-(2-carboxyethyl)-5-methoxy]benzyl]-[2-(2-carboxyethyl)-5-methoxy]benzyl]-4-methoxy-2-methylhydrocinnamic acid

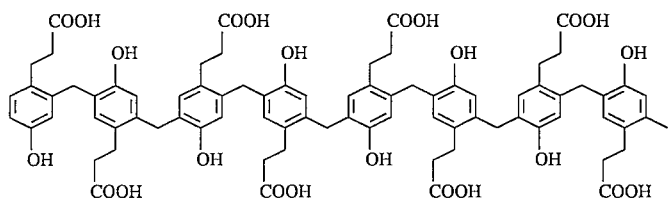

2-(2-methoxycarbonylethyl)-4-[4-[4-[4-[4-[4-[[2-(2-methoxycarbonylethyl)-5-trimethylacetyl]oxybenzyl]-[2-(2-methoxycarbonylethyl)-5-methoxy]benzyl]-[2-(2-methoxycarbonylethyl)-5-methoxy]benzyl]-[2-(2-methoxycarbonylethyl)-5-methoxy]benzyl]-[2-(2-methoxycarbonylethyl)-5-methoxy]benzyl]-[2-(2-methoxycarbonylethyl)-5-methoxy]benzyl]-[2-(2-methoxycarbonylethyl)-5-methoxy]benzyl]-5-methoxy-benzyloxy-tert-butyldimethylsilane

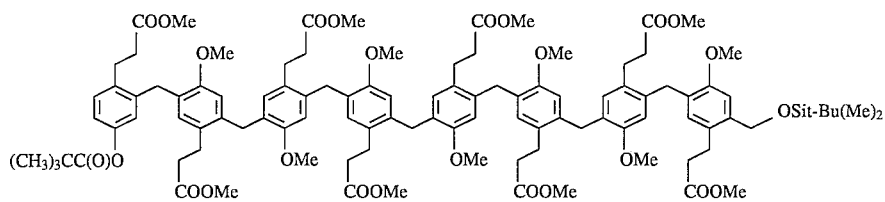

1,2-bis-[4-[4-[4-[[2-(2-methoxycarbonylethyl)-5-trimethylacetyl]oxybenzyl]-[2-(2-methoxycarbonylethyl)-5-methoxy]benzyl]-[2-(2-methoxycarbonylethyl)-5-methoxy]benzyl]-[2-(2-methoxycarbonylethyl)-5-methoxy]phenyl]ethane

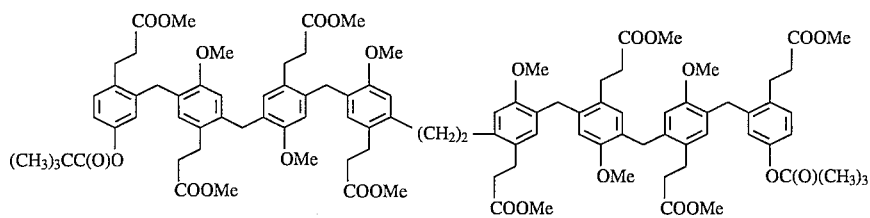

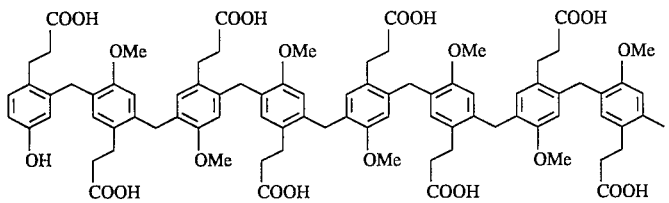

5-[4-[4-[4-[4-[4-[4-[4-[4-[4-[4-[4-[4-[4-[[2-(2-carboxy-ethyl)-5-hydroxy]benzyl]-[2-(2-carboxyethyl)-5-hydroxy]benzyl]-[2-(2-carboxyethyl)-5-hydroxy]benzyl]-[2-(2-carboxyethyl)-5-hydroxy]benzyl]-[2-(2-carboxyethyl)-5-hydroxy]benzyl]-[2-(2-carboxyethyl)-5-hydroxy]benzyl]-[2-(2-carboxyethyl)-5-hydroxy]benzyl]-[2-(2-carboxyethyl)-5-hydroxy]benzyl]-[2-(2-carboxyethyl)-5-hydroxy]benzyl]-[2-(2-carboxyethyl)-5-hydroxy]benzyl]-[2-(2-carboxyethyl)-5-hydroxy]benzyl]-[2-(2-carboxyethyl)-5-hydroxy]benzyl]-[2-(2-carboxyethyl)-5-hydroxy]benzyl]-4-hydroxy-2-methylhydrocinnamic acid benzyl]-[2-(2-carboxyethyl)-5-methoxy]benzyl]-[2-(2-carboxyethyl)-5-methoxy]benzyl]-[2-(2-carboxyethyl)-5-methoxy]benzyl]-[2-(2-carboxyethyl)-5-methoxy]benzyl]-[2-(2-carboxyethyl)-5-methoxy]benzyl]-[2-(2-carboxyethyl)-5-methoxy]benzyl]-[2-(2-carboxyethyl)-5-methoxy]benzyl]-[2-(2-carboxyethyl)-5-methoxy]benzyl]-[2-(2-carboxyethyl)-5-methoxy]benzyl]-[2-(2-carboxyethyl)-5-methoxy]benzyl]-4-hydroxy-2-methylhydrocinnamic acid

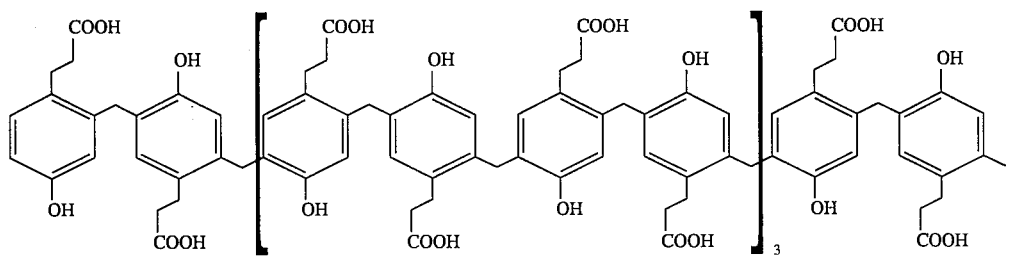

1,2-bis-[4-[4-[4-[4-[4-[4-[[2-(2-carboxyethyl)-5-hydroxy]benzyl]-[2-(2-carboxyethyl)-5-methoxy]benzyl]-[2-(2-carboxyethyl)-5-methoxy]benzyl]-[2-(2-carboxyethyl)-5-methoxy]benzyl]-[2-(2-carboxyethyl)-5-methoxy]benzyl]-[2-(2-carboxyethyl)-5-methoxy]benzyl]-[2-(2-carboxyethyl)-5-methoxy]benzyl]-[2-(2-carboxyethyl)-5-methoxy]phenyl]ethane

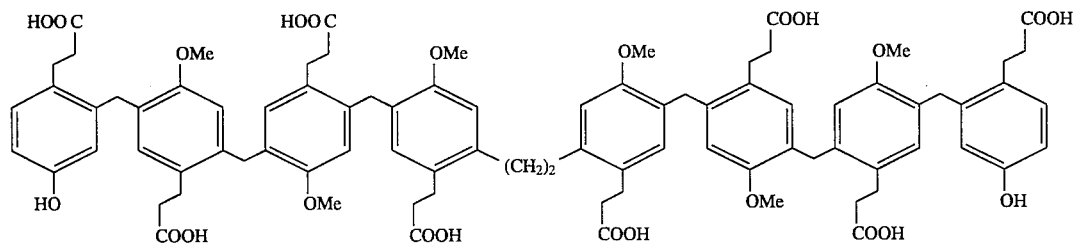

5-[4-[4-[4-[4-[4-[4-[4-[4-[4-[4-[4-[4-[4-[[2-(2-carboxyethyl)-5-hydroxy]benzyl]-[2-(2-carboxyethyl)-5-methoxy]benzyl]-[2-(2-carboxyethyl)-5-methoxy]benzyl]-[2-(2-carboxyethyl)-5-methoxy]benzyl]-[2-(2-carboxyethyl)-5-methoxy]benzyl]-[2-(2-carboxyethyl)-5-methoxy]benzyl]-[2-(2-carboxyethyl)-5-methoxy]

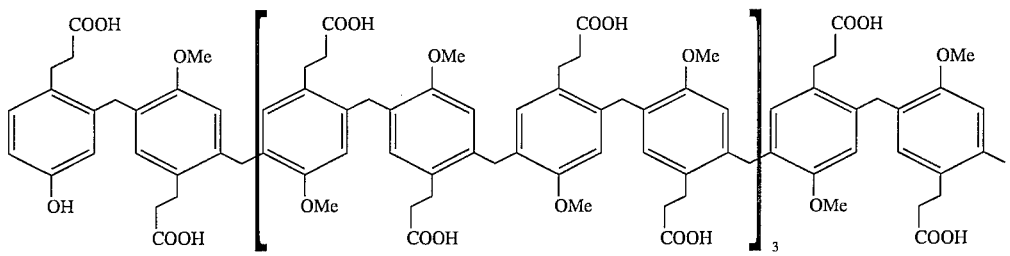

methyl-5-acetoxy-2-[4-[4-[4-[4-[4-[[5-(2 -methoxycarbonylethyl)-4 -hydroxymethyl-2-methoxy]phenoxymethyl]-[5-(2-methoxycarbonylethyl)-2 -methoxy]phenoxymethyl]-[5-(2-methoxycarbonylethyl)-2 -methoxy]phenoxymethyl]-[5-(2-methoxycarbonylethyl)-2 -methoxy]phenoxymethyl]-[5-(2-methoxycarbonylethyl)-2 -methoxy]phenoxymethyl]-[5-(2-methoxycarbonylethyl)-2 -methoxy]phenoxymethyl]-[5-(2-methoxycarbonylethyl)-2 -methoxy]phenoxymethyl]-4-methoxyhydrocinnamate 2-methoxy]phenoxymethyl]-[5-(2 -methoxycarbonylethyl)-2-methoxy]phenoxymethyl]-4-methoxyhydrocinnamate

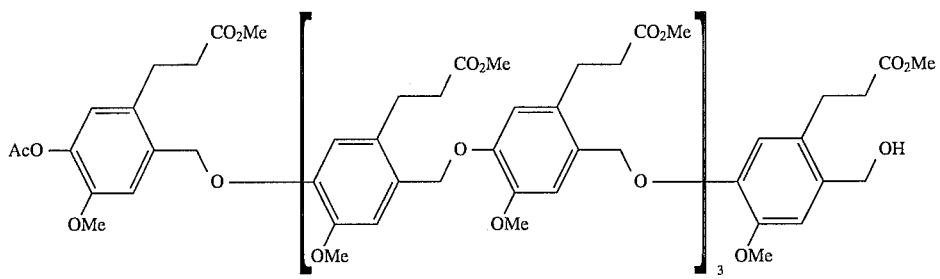

and

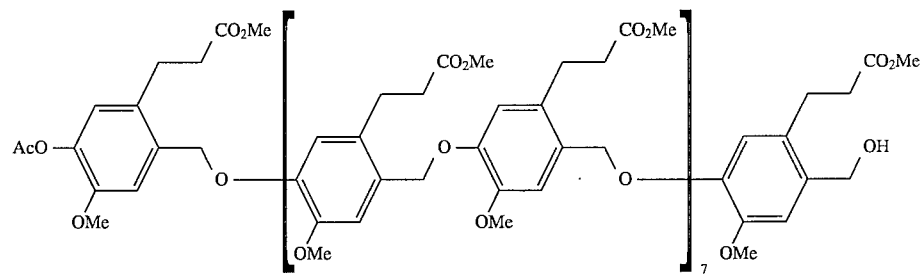

methyl-5-acetoxy-2-[4-[4-[4-[4-[4-[4-[4-[4-[4 -[4-[4-[4-[4-[[5-(2 -methoxycarbonylethyl)-4-hydroxymethyl-2-methoxy]phenoxymethyl]-[5-(2 -methoxycarbonylethyl)-2-methoxy]phenoxymethyl]-[5-(2 -methoxycarbonylethyl)-2-methoxy]phenoxymethyl]-[5-(2-methoxycarbonylethyl)-2-methoxy]phenoxymethyl]-[5-(2 -methoxycarbonylethyl)-2-methoxy]phenoxymethyl]-[5-(2 -methoxycarbonylethyl)-2-methoxy]phenoxymethyl]-[5-(2 -methoxycarbonylethyl)-2-methoxy]phenoxymethyl]-[5-(2 -methoxycarbonylethyl)-2-methoxy]phenoxymethyl]-[5-(2-methoxycarbonylethyl)-2-methoxy]phenoxymethyl]-[5-(2 -methoxycarbonylethyl)-2-methoxy]phenoxymethyl]-[5-(2 -methoxycarbonylethyl)-2-methoxy]phenoxymethyl]-[5-(2 -methoxycarbonylethyl)-2-methoxy]phenoxymethyl]-[5-(2 -methoxycarbonylethyl)-

Compounds of the present invention may contain asymmetric centers. These asymmetric centers may independently be in either the R or S configuration. The present invention comprises the individual stereoisomers and mixtures thereof.

The compounds of the present invention may be useful in the form of the free base or acid or in the form of a pharmaceutically acceptable salt thereof. All forms are within the scope of the invention.

Where the compound of the present invention is substituted with one or more basic moieties, acid addition salts may be formed and are simply a more convenient form for use; and in practice, use of the salt form inherently amounts to use of the free base form. The acids which can be used to prepare the acid addition salts include preferably those which produce, when combined with the free base, pharmaceutically acceptable salts, that is, salts whose anions are non-toxic to the animal organism in pharmaceutical doses of the salts, so that the beneficial properties inherent in the free base are not vitiated by side effects ascribable to the anions. Although pharmaceutically acceptable salts of said basic compounds are preferred, all acid addition salts are useful as sources of the free base form even if the particular salt, per se, is desired only as an intermediate product as for example, when the salt is formed only for purposes of purification, and identification, or when it is used as intermediate in preparing a pharmaceutically acceptable salt by ion exchange procedures. Pharmaceutically acceptable salts within the scope of the invention are those derived from the following acids: mineral acids such as hydrochloric acid, sulfuric acid, phosphoric acid and sulfamic acid; and organic acids such as acetic acid, citric acid, lactic acid, tartaric acid, malonic acid, methanesufonic acid, ethanesulfonic acid, benzenesulfonic acid, p-toluenesulfonic acid, cyclohexylsulfamic acid, quinic acid, and the like. The corresponding acid addition salts comprise the following: hydrochloride, sulfate, phosphate, sulfamate, acetate, citrate, lactate, tartarate, malonate, methanesulfonate, ethanesulfonate, benzenesulfonate, p-toluenesulfonate, cyclohexylsulfamate and quinate, respectively.

The acid addition salts of the compounds of this invention are prepared either by dissolving the free base in aqueous or aqueous-alcohol solution or other suitable solvents containing the appropriate acid and isolating the salt by evaporating the solution, or by reacting the free base and acid in an organic solvent, in which case the salt separates directly or can be obtained by concentration of the solution.

Where the compound of the invention is substituted by one or more acidic moieties, base addition salts may be formed and are simply a more convenient form for use; and in practice, use of the salt form inherently amounts to use of the free acid form. The bases which can be used to prepare the base addition salts include preferably those which produce, when combined with the free acid, pharmaceutically acceptable salts, that is, salts whose cations are non-toxic to the animal organism in pharmaceutical doses of the salts, so that the beneficial properties inherent in the free acid are not vitiated by side effects ascribable to the cations. Pharmaceutically acceptable salts within the scope of the invention are those derived from the following bases: sodium hydroxide, potassium hydroxide, calcium hydroxide, aluminum hydroxide, lithium hydroxide, magnesium hydroxide, zinc hydroxide, ammonia, ethylenediamine, N-methyl-glucamine, lysine, arginine, ornithine, choline, N,N'-dibenzylethylenediamine, chloroprocaine, diethanolamine, procaine, N-benzylphenethylamine, diethylamine, piperazine, tris(hydroxymethyl)aminomethane, tetramethylammonium hydroxide, and the like.

Metal salts of compounds of the present invention may be obtained by contacting a hydroxide, carbonate or similar reactive compound of the chosen metal in an aqueous solvent with the free acid form of the compound. The aqueous solvent employed may be water or it may be a mixture of water with an organic solvent, preferably an alcohol such as methanol or ethanol, a ketone such as acetone, an aliphatic ether such as tetrahydrofuran, or an ester such as ethyl acetate. Such reactions are normally conducted at ambient temperature but they may, if desired, be conducted with heating.

Amine salts of compounds of the present invention may be obtained by contacting an amine in an aqueous solvent with the free acid form of the compound. Suitable aqueous solvents include water and mixtures of water with alcohols such as methanol or ethanol, ethers such as tetrahydrofuran, nitriles such as acetonitrile, or ketones such as acetone. Amino acid salts may be similarly prepared.

Compounds of this invention may be prepared in accordance with the reaction sequences described below, or can be prepared by methods known in the art. The starting materials used in the preparation of compounds of this invention are known or are commercially available, or can be prepared by known methods or by specific reaction schemes described herein.

The oligomeric compounds of the present invention are generally available by a series of reactions whereby monomeric or oligomeric precursors are sequentially coupled together and/or modified to prepare the desired compound.

If it is necessary or desirable to prevent cross-reaction between chemically active substituents on the monomeric or oligomeric precursor compounds, either during coupling reactions or at other points in the reaction sequence, the substituents may be protected by standard blocking groups which may be retained or subsequently removed, as required, by known methods to afford the desired product or precursor (see, for example, Green, "Protective Groups in Organic Synthesis", Wiley, New York, 1981).

A preferred method of preparation of compounds of the present invention is shown in Scheme I below.

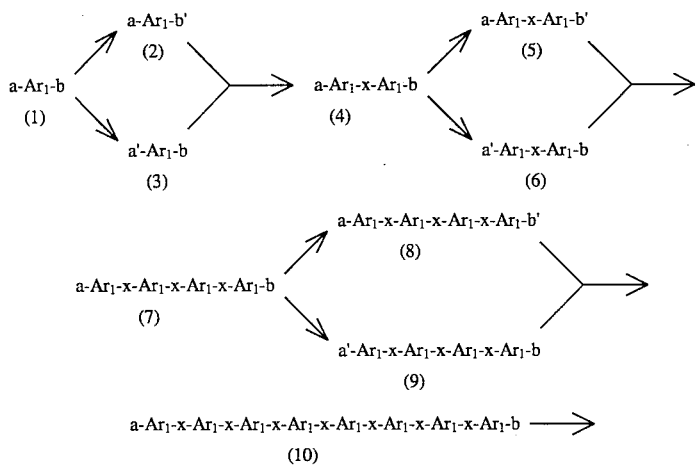

-continued
Scheme I

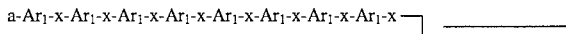
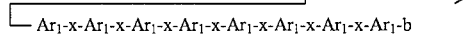
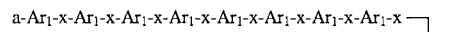

(11)

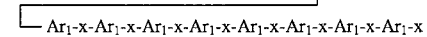
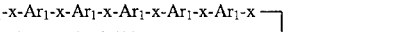

(12)

Ar$_1$ represents an aromatic carbocyclic or aromatic heterocyclic ring containing the substituent groups desired in the final oligomeric product, or protected derivatives thereof, or precursor moieties thereto. Ar$_1$ also contains the substituent groups a and b, which groups may be selectively and independently converted to groups a' and b', which groups a' and b' are such so as to form a linking group x between the aromatic groups when subjected to the appropriate reaction conditions.

The dimeric precursor (4) is likewise selectively converted to the two separate dimeric precursors (5) and (6) which contain the substituent groups b' and a', respectively. (5) and (6) are then reacted together to form the tetramer (7). This sequence is repeated to prepare the octomer (10), hexadecamer (11), and the 32-membered oligomer (12).

This method of preparation is also used to prepare compounds of the present invention containing non-identical monomeric residues. An example of this is shown in Scheme II below.

Scheme II

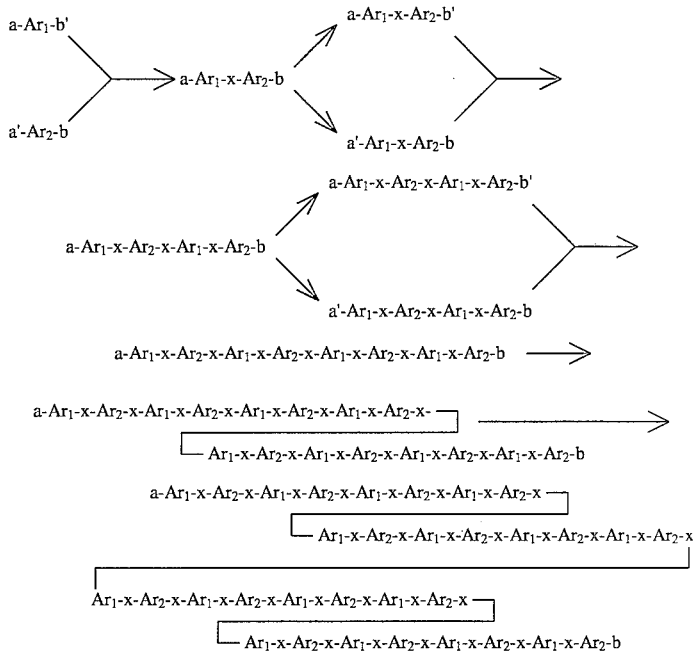

In Scheme I, the monomeric precursor (1) is converted to two separate monomeric precursors (2) and (3) by chemical modification of the substitutent groups b and a, respectively. Precursor (2) has a substituent moiety b' which is chemically reactive toward a substituent moiety a' on precursor (3). (2) and (3) are then reacted together to give the dimer (4), the two monomeric residues being connected by the linking group x.

In Scheme II, two different monomeric precursors are coupled as above and the resulting dimer carried on as in Scheme I to give oligomers having repeating units of the dimer.

It should be apparent that different monomeric or oligomeric precursors (i.e. monomeric or oligomeric precursors containing different aromatic rings or containing different substituent groups or protected derivatives or precursor moieties thereto, or oligomeric precursors containing varying numbers of monomeric units) may be introduced at any stage in the above Schemes to effect preparation of oligomers containing any desired number of monomeric residues, each having any desired substituent groups. It should also be apparent that the nature of the linking group x at a given point in the oligomer may be varied by varying the nature of the groups a' and b'.

An exemplary preparation scheme is shown in Scheme III below.

The resulting aryl iodide and benzyl bromide then may be coupled, for example by treatment with zinc and 1,2-dibromoethane, in the presence of tetrakis(triphenylphosphine)palladium, in an aprotic organic solvent, for example tetrahydrofuran, to form the dimeric product. In this example the linking group so formed is the methylene group.

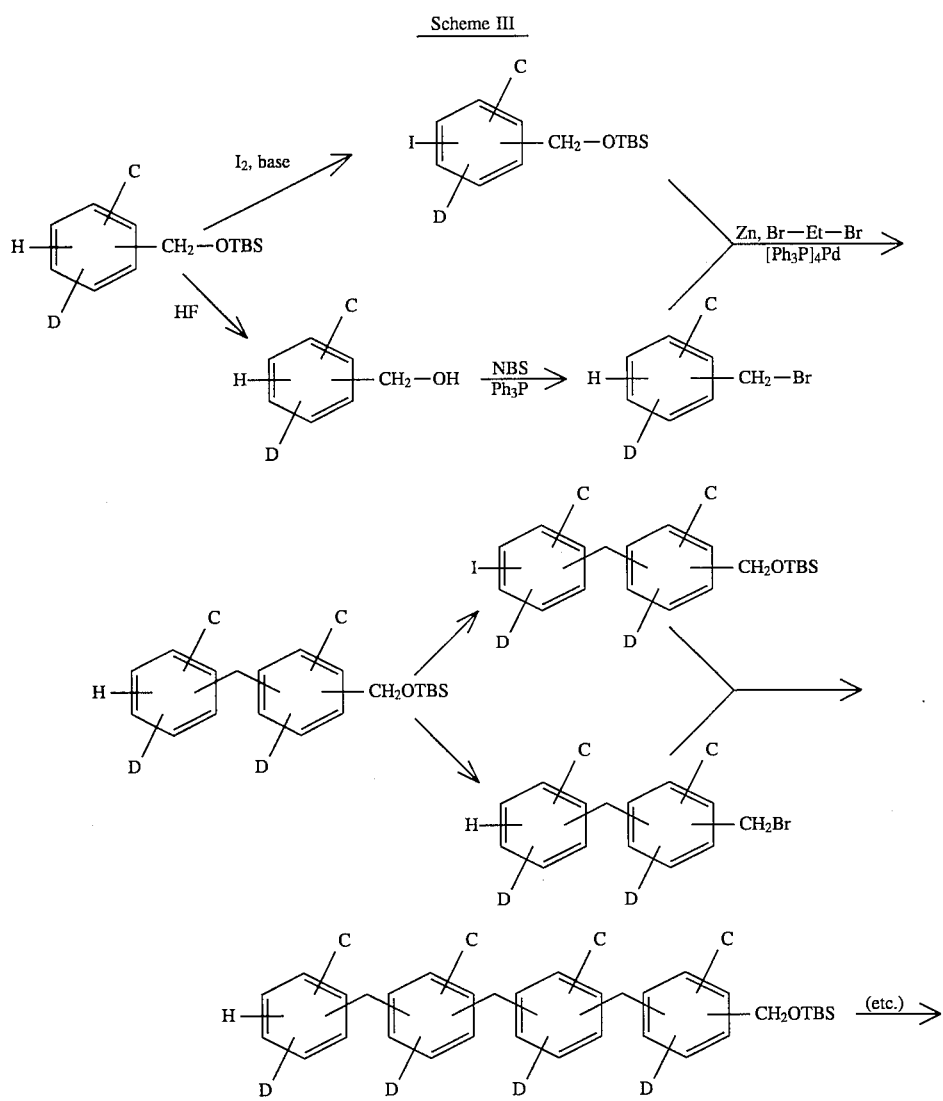

In Scheme III a monomeric precursor benzyl alcohol, protected as the tert-butyldimethylsilyl ether, and substituted with substituent groups C and D, which may be the substituent groups desired in the final product or may be protected derivatives thereof or precursor substituents thereto, is treated with iodine in the presence of an organic base, for example morpholine, in an organic solvent, for example methylene chloride, to give the aryl iodide.

The monomeric precursor silyl ether, in a separate step, is deprotected by treatment with 48% hydrofluoric acid in an aprotic organic solvent, for example acetonitrile, to prepare the benzyl alcohol. The benzyl bromide is then prepared by treatment of the benzyl alcohol with N-bromosuccinimide in the presence of triphenylphosphine in an aprotic organic solvent, for example tetrahydrofuran.

The resulting dimeric silyl ether may then be sequentially converted to the analgous aryl iodide and benzyl bromide and these dimeric products coupled, as above, to prepare the analogous tetramer. This sequence may be repeated, as required, to prepare the oligomer of desired length. The substituent groups C and D may then be deprotected or modified, if necessary or desired, to prepare the compound of the present invention.

Another exemplary preparation is shown in Scheme IV below.

Scheme IV

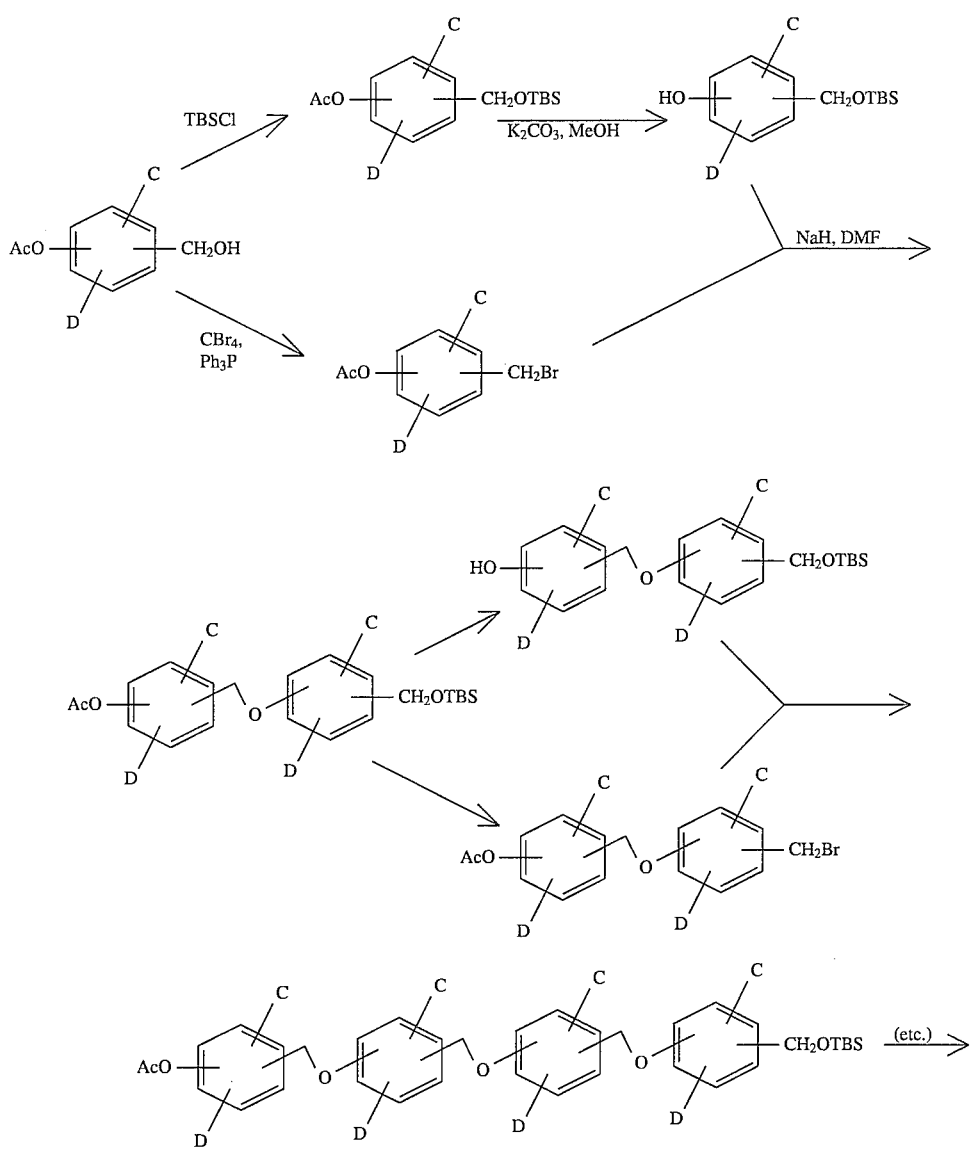

The appropriately substituted acetoxy benzyl alcohol is converted to the tert-butyldimethylsilyl ether by treatment with tert-butylchlorodimethylsilane in an aprotic organic solvent, for example methylene chloride. The acetyl group is then removed by treatment with potassium carbonate in a polar organic solvent such as methanol to prepare the corresponding phenol.

The acetoxy benzyl alcohol is separately converted to the benzyl bromide by treatment with carbon tetrabromide in the presence of triphenylphosphine in an aprotic organic solvent, for example tetrahydrofuran.

The resulting benzyl bromide and phenol are coupled by treatment with a strong base, for example sodium hydride, in a polar aprotic organic solvent, for example dimethylformamide to prepare the dimeric precursor. In this example the linking group so formed is the oxymethyl group.

The resulting dimeric silyl ether may then be sequentially converted to the analgous phenol and benzyl bromide and these dimeric products coupled, as above, to prepare the analogous tetramer. This sequence may be repeated, as required, to prepare the oligomer of desired length. The substituent groups C and D may then be deprotected or modified, if necessary or desired, to prepare the compound of the present invention.

The methods of preparation of compounds of the present invention discussed above allow the formation of essentially pure oligomeric intermediates or final products, each having specific composition and length, in high yield. Compounds of the present invention may also be prepared treating monomeric precursors under conditions, known in the art, which cause the precursors to condense or couple with each other to form a mixture of oligomers which may then be separated by standard methods to give the desired products. An exemplary preparation of this kind is shown in Scheme V below.

Scheme V

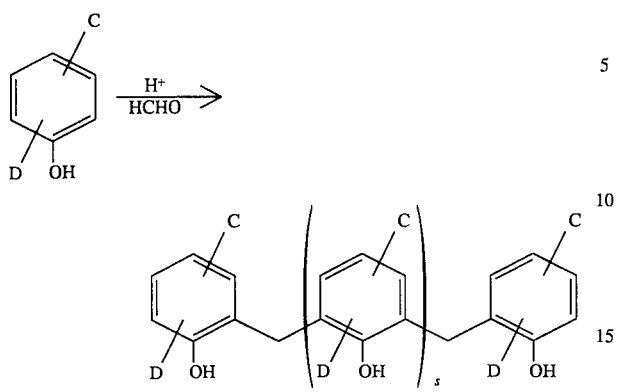

An appropriately substituted phenol is treated with formalin in the presence of a mineral acid, for example sulfuric acid, in methanol to give a mixture of products which includes oligomers of the desired composition, being phenolic monomers linked by methylene groups, and containing the desired number, s+2, of monomeric units. The individual components of the mixture are then isolated by standard methods, for example flash chromatography or HPLC.

The present invention is further explained by the following illustrative examples.

EXAMPLE 1

Preparation of
Bis-[5-(2-carboxyethyl)-3-[5-(2-carboxyethyl)-
2-hydroxybenzyl]2 -hydroxyphenyl]methane

Step 1: Preparation of Methyl 3-(4-Hydroxyphenyl) Propionate

A solution of p-hydroxycinnamic acid (32.8 g) in methanol (200 ml) is hydrogenated over 5% palladium on carbon (0.5 g) until hydrogen uptake ceases. The catalyst is removed by filtration and sulfuric acid (1 ml) added to the filtrate and the resulting solution stirred at reflux for about 18 hours. The solution is concentrated in vacuo, the residue dissolved in ether and the solution washed with water, saturated sodium bicarbonate solution, and brine. The organic solution is concentrated in vacuo to give the desired product.

Step 2: Preparation of Bis-[5-(2-methoxycarbonylethyl)-3-[5-(2-methoxycarbonylethyl)-2-hydroxybenzyl] 2-hydroxyphenyl]methane A solution of methyl 3-(4-hydroxyphenyl) propionate (4.68 g) in methanol (8 ml) is cooled to 0° C. and sulfuric acid (16 ml) is cautiously added. The temperature is allowed to return to 0° C. and a solution of 37% aqueous formaldehyde (0.80 ml) in methanol (1 ml) is added dropwise over about 4 hours. The mixture is stirred at room temperature for about 18 hours, poured over ice, this mixture is extracted with ethyl acetate, and the ethyl acetate solution concentrated in vacuo. The crude product is flash chromatographed over silica gel, eluting with 50% ethyl acetate in hexane. The mixture of oligomers so obtained is purified by preparative HPLC to give the desired product.

Step 3: Preparation of Bis-[5-(2-carboxyethyl)-3-[5-(2-carboxyethyl)-2-hydroxybenzyl]2-hydroxyphenyl]methane A solution of bis-[5-(2-methoxycarbonylethyl)-3-[5-(2-methoxycarbonylethyl)-2-hydroxybenzyl]2-hydroxyphenyl]methane (0.10 g) in methanol (2 ml) is stirred with 10% aqueous sodium hydroxide (NaOH) (1 ml) at room temperature. The mixture is quenched with dilute aqueous hydrochloric acid (HCl) and the organic soluble material retreated as above. The mixture is quenched as above and the organic soluble material flash chromatographed, eluting with 10% methanol in chloroform. The product so obtained is treated with ammonium hydroxide solution and lyophilized to give the desired product as the ammonium salt, m.p. 150° C. (dec.).

EXAMPLE 2

Preparation of
5-[4-[4-[4-[4-[4-[4-[4-[4-[4-[4-[4-[4-[4-[[2-
(2-Carboxyethyl)-5-hydroxy]benzyl]-[2-
(2-carboxyethyl)-5-hydroxy]benzyl]-[2
-(2-carboxyethyl)-5-
hydroxy]benzyl]-[2-(2-carboxyethyl)-
5-hydroxy]benzyl]-[2-(2-carboxyethyl)-5-
hydroxy]benzyl]-[2-(2-carboxyethyl)-
5-hydroxy]benzyl]-[2-(2-carboxyethyl)-5-
hydroxy]benzyl]-[2-(2-carboxyethyl)-
5-hydroxy]benzyl]-[2-(2-carboxyethyl)-5-
hydroxy]benzyl]-[2-(2-carboxyethyl)-
5-hydroxy]benzyl]-[2-(2-carboxyethyl)-5-
hydroxy]benzyl]-[2-(2-carboxyethyl)-
5-hydroxy]benzyl]-[2-(2-carboxyethyl)-5-
hydroxy]benzyl]-[2-(2-carboxyethyl)-
5-hydroxy]benzyl]-[2-(2-carboxyethyl)-5-
hydroxy]benzyl]-4-hydroxy-2-methylhydrocinnamic
Acid

Step 1: Preparation of 2-Bromo-5-trimethylacetyloxybenzaldehyde

To a suspension of 3-hydroxybenzaldehyde (36.0 g) in chloroform (800 ml) is added a solution of bromine (15.8 ml) in chloroform (60 ml) over a period of about 2.5 minutes. The mixture is stirred for 5 minutes, washed with dilute sodium bicarbonate solution, then water, and the organic solution is dried over magnesium sulfate, filtered and concentrated in vacuo. Dry toluene is azeotroped from the residue and this residue is dissolved in methylene chloride (700 ml). To this solution is added triethylamine (55 ml), trimethylacetic anhydride (70 ml), and 4-dimethylaminopyridine (DMAP) (2.0 g). The solution is stirred for 14 hours, diluted with ether, and washed with water, then brine. The organic solution is dried over magnesium sulfate, concentrated in vacuo and the residue purified by flash chromatography, eluting with 5% ether in hexanes, to give the desired product.

Step 2: Preparation of 2-Tert-butyldimethylsilyloxymethyl-4-trimethylacetyloxybromobenzene A solution of 2-bromo-5-trimethylacetyloxybenzaldehyde (52 g) is tetrahydrofuran (THF) (400 ml) is cooled to −78° C. and 0.5M sodium borohydride in diglyme (182 ml) is added. The solution is stirred at room temperature for 20 minutes, quenched with 1M HCl (200 ml), and diluted with ether. The ether solution is washed with six portions of water, dried over magnesium sulfate, filtered, and concentrated in vacuo. Dry toluene is azeotroped from the residue and this residue is dissolved in anhydrous dimethylformamide (DMF) (400 ml) and imidazole (15 g), tert-butyldimethylchlorosilane (30 g) and DMAP (1.26 g) are added. The solution is stirred for 30 minutes, diluted with ether and the ether solution washed with water, dried over magnesium sulfate, filtered and concentrated in vacuo. The residue is purified by flash chromatography, eluting with 2% ether in hexanes, to give the desired product.

Step 3: Preparation of Methyl 2-Tert-butyldimethylsilyloxymethyl-4-trimethylacetyloxycinnamate To a solution of 2-tert-butyldimethylsilyloxymethyl-4-trimethylacetyloxybromobenzene (48 g) in dry dimethylformamide (460 ml) is added bis(triphenylphosphine)palladium dichloride (2.5 g). The resulting solution is degassed and dry triethylamine (67 ml) added, followed by methyl acrylate (42.6 ml). The resulting solution is stirred at 135° C. for about 1 hour, cooled, diluted with ether, washed with water, dried over magnesium sulfate, filtered, then concentrated under reduced pressure. The residue is purified by flash chromatography, eluting with 10% ether in hexanes, to give the desired product.

Step 4: Preparation of Methyl 2-Tert-butyldimethylsilyloxymethyl-4-trimethylacetyloxyhydrocinnamate A solution of methyl 2-tert-butyldimethylsilyloxymethyl-4 -trimethylacetyloxycinnamate (40.8 g) and tris-(triphenylphosphine)rhodium chloride (2.5 g) in dry benzene (500 ml) is degassed, then stirred under an atmosphere of hydrogen at 40° C. for 48 hours. The hydrogen atmosphere is replaced by nitrogen and the solution concentrated in vacuo. The residue is diluted with ether and the mixture filtered, and the filtrate concentrated in vacuo to give the desired product.

Step 5: Preparation of Methyl 2-Tert-butyldimethylsilyloxymethyl-4-hydroxy-5-iodohydrocinnamate A solution of methyl 2-tert-butyldimethylsilyloxymethyl-4 -trimethylacetyloxy hydrocinnamate (8.16 g) and 25% sodium methoxide in methanol (3.9 ml) in methanol (40 ml) is stirred at room temperature for 30 minutes and diluted with ether. The ether solution is washed with 1M hydrochloric acid, brine, dried over magnesium sulfate, concentrated in vacuo and the residue dissolved in methylene chloride (145 ml). To this solution is added morpholine (4.25 g), then iodine (6.09 g) and the resulting suspension stirred at room temperature for 2 hours and diluted with ether. The ether solution is washed with 1M HCl (25 ml), then brine, dried over magnesium sulfate, filtered, and concentrated in vacuo. The residue is purified by flash chromatography, eluting with 15% ether in hexanes, to give the desired product.

Step 6: Preparation of Methyl 2-Tert-butyldimethylsilyloxymethyl-4-methoxy-5-iodohydrocinnamate A suspension of 60% sodium hydride in mineral (1.2 g) in THF (56 ml) is cooled to −20° C. and of solution of methyl 2-tert-butyldimethylsilyloxymethyl-4 -hydroxy-5-iodohydrocinnamate (12.6 g), iodomethane (5 ml) and 1,3-dimethyl-3,4,5,6-tetrahydro-2(1H)-pyrimidinone (DMPU) (8 ml) in THF (20 ml) is added. The cold bath is removed, the mixture stirred for about 2 hours, and diluted with ether. The ether solution is washed with 0.1M HCl, brine, dried over magnesium sulfate, filtered and concentrated in vacuo. The residue is purified by flash chromatography, eluting with 10% ether in hexanes, to give the desired product.

Step 7: Preparation of Methyl 2-Hydroxymethyl-4-trimethylacetyloxy Hydrocinnamate To a solution of methyl 2-tert-butyldimethylsilyloxymethyl-4 -trimethylacetyloxyhydrocinnamate (32.6 g) in acetonitrile (350 ml) is added 48% hydrofluoric acid (4.6 ml) and the solution stirred at room temperature for 40 minutes, the diluted with ether. The ether solution is washed with water, dilute sodium bicarbonate solution, brine, dried over magnesium sulfate, and concentrated in vacuo. To the residue is added triethylamine (5 ml) and this purified by flash chromatography, eluting with 60% ether in hexanes, to give the desired product.

Step 8: Preparation of Methyl 2-Bromomethyl-4-trimethylacetyloxyhydrocinnamate To a solution of 2-hydroxymethyl-4-trimethylacetyloxy hydrocinnamate (22.6 g) in THF (800 ml) is added triphenylphosphine (31.4 g), then recrystallized N-bromosuccinimide (20 g). The mixture is stirred for about 15 minutes, concentrated in vacuo, and the residue purified by flash chromatography, eluting with 30% ether in hexanes, to give the desired product.

Step 9: Preparation of Methyl 2-Tert-butyldimethylsilyloxymethyl-4-methoxy-5-[2-(2-methoxycarbonylethyl)-5-trimethylacetyloxy] benzyl Hydrocinnamate To a suspension of zinc dust (3.64 g) in THF (4 ml) is added freshly distilled 1,2-dibromoethane and the mixture is warmed to reflux, stirred for about 1 minute, then cooled to −5° C. A solution of 2-bromomethyl-4 -trimethylacetyloxy-hydrocinnamate (8.28 g) in THF (20 ml) is added over about 1.3 hours, and the mixture is stirred for and additional 30 minutes. Stirring is stopped and the solid allowed to settle. The supernatent liquid is transferred via cannula to a solution of methyl 2-tert-butyldimethylsilyloxymethyl-4 -methoxy-5-iodo hydrocinnamate (9.26 g) and tetrakis(triphenylphosphine)palladium (1.17 g) in THF (40 ml). The resulting solution is stirred at 60° C. for about 2 hours, diluted with ether, washed with 5% aqueous ammonia, the brine. The ether solution is dried over magnesium sulfate, concentrated in vacuo, and the residue purified by flash chromatography, eluting with a gradient of 20% to 30% ether in hexanes to give the desired product.

Step 10: Preparation of Methyl 2-Tert-butyldimethylsilyloxymethyl-4-methoxy-5-[2-(2-methoxycarbonylethyl)-5-hydroxy-4-iodo] benzyl Hydrocinnamate Using essentially the procedure of Example 2, Step 5, and purifying the crude product by flash chromatography, eluting with a gradient of 20% to 25% ether in hexanes, the desired product is prepared from methyl 2-tert-butyldimethylsilyloxymethyl- 4-methoxy-5-[2-(2-methoxycarbonylethyl)-5 -trimethylacetyloxy]benzyl hydrocinnamate.

Step 11: Preparation of Methyl 2-Tert-butyldimethylsilyloxymethyl-4-methoxy-5-[2-(2-methoxycarbonylethyl)-5-methoxy-4-iodo]benzyl Hydrocinnamate Using essentially the procedure of Example 2, Step 6, and purifying the crude product by flash chromatography, eluting with a gradient of 20% to 25% ether in hexanes, the desired product is prepared from methyl 2-tert-butyldimethylsilyloxymethyl- 4-methoxy-5-[2-(2-methoxycarbonylethyl)-5 -hydroxy-4-iodo]benzyl hydrocinnamate.

Step 12: Preparation of Methyl 2-hydroxymethyl-4-methoxy-5-[2-(2-methoxycarbonylethyl)-5-trimethylacetyloxy]benzylhydrocinnamate Using essentially the procedure of Example 2, Step 7, and purifying the crude product by flash chromatography, eluting with a gradient of 60% to 80% ether in hexanes, the desired product is prepared from methyl 2-tert-butyldimethylsilyloxymethyl- 4-methoxy-5-[2-(2-methoxycarbonylethyl)-5 -trimethylacetyloxy]benzyl hydrocinnamate.

Step 13: Preparation of Methyl 2-Bromomethyl-4-methoxy-5-[2-(2-methoxycarbonylethyl)-5-trimethylacetyloxy]benzylhydrocinnamate Using essentially the procefure of Example 2, Step 8, and purifying the crude product by flash chromatography, eluting with 40% ether in hexanes, the desired product is prepared from methyl 2-hydroxymethyl-4-methoxy-5-[2-(2 -methoxycarbonylethyl)-5-trimethylacetyloxy]benzyl hydrocinnamate.

Step 14: Preparation of Methyl 5-[4-[4-[[2-(2-methoxycarbonylethyl)-5 -trimethylacetyloxy]benzyl]-[2-(2-methoxycarbonylethyl)-5-methoxy]benzyl]-[2 -(2-methoxycarbonylethyl)-5-methoxy]benzyl]-4-methoxy-2-tert-butyldimethylsilyloxymethylhydrocinnamate Using essentially the procedure of Example 2, Step 9, and purifying the crude product by flash chromatography, eluting with ether/methylene chloride/hexane (4:1:5), the desired product is prepared from 2-bromomethyl-4-methoxy-5-[2-(2-methoxycarbonylethyl)-5-trimethylacetyloxy]benzyl hydrocinnamate and methyl 2-tert-butyldimethylsilyloxymethyl-4-methoxy-5-[2 -(2-methoxycarbonylethyl))-5-methoxy-4-iodo]benzyl hydrocinnamate.

A second product, 1,2-bis-[2-(2-methoxycarbonylethyl)-4-[2-(2 -methoxycarbonylethyl)-5-trimethylacetyloxybenzyl]-5-methoxyphenyl]ethane, is also isolated.

Step 15: Preparation of Methyl 5-[4-[4-[[2-(2-Methoxycarbonylethyl)-5-trimethylacetyloxy]benzyl]-[2-(2-methoxycarbonylethyl)-5-methoxy]benzyl]-[2 -(2-methoxycarbonylethyl)-5-methoxy]benzyl]-4-methoxy-2-hydroxymethylhydrocinnamate Using essentially the procedure of Example 2, Step 7, and purifying the crude product by flash chromatography, eluting with 90% ether in methylene chloride, the desired product is prepared from methyl 5-[4-[4-[[2-(2 -methoxycarbonylethyl)-5-trimethylacetyloxy]benzyl]-[2-(2 -methoxycarbonylethyl)-5-methoxy]benzyl]-[2-(2-methoxycarbonylethyl)-5 -methoxy]benzyl]-4-methoxy-2-tert-butyldimethylsilyloxymethylhydrocinnamate.

Step 16: Preparation of Methyl 5-[4-[4-[[2-(2-Methoxycarbonylethyl)-5-trimethylacetyloxy]benzyl]-[2-(2-methoxycarbonylethyl)-5-methoxy]benzyl]-[2-(2-methoxycarbonylethyl)-5-methoxy]benzyl]-4-methoxy-2 -bromomethylhydrocinnamate Using essentially the procedure of Example 2, Step 8, and purifying the crude product by flash chromatography, eluting with ether/methylene choride/hexanes (4:1:5), the desired product is prepared from methyl 5-[4-[4 -[[2-(2-methoxycarbonylethyl)-5-trimethylacetyloxy]benzyl]-[2-(2 -methoxycarbonylethyl)-5-methoxy]benzyl]-[2-(2-methoxycarbonylethyl)-5 -methoxy]benzyl]-4-methoxy-2-hydroxymethylhydrocinnamate.

Step 17: Preparation of Methyl 5-[4-[4-[[2-(2-Methoxycarbonylethyl)-5-hydroxy-4-iodo]benzyl]-[2-(2-methoxycarbonylethyl)-5-methoxy]benzyl]-[2-(2-methoxycarbonylethyl)-5-methoxy]benzyl]-4-methoxy-2-tert-butyldimethylsilyloxymethylhydrocinnamate Using essentially the procedure of Example 2, Step 5, and purifying the crude product by flash chromatography, eluting with ether/methylene chloride/hexanes (3:1:6), the desired product is prepared from methyl 5-[4-[4 -[[2-(2-methoxycarbonylethyl)-5-trimethylacetyloxy]benzyl]-[2-(2 -methoxycarbonylethyl)-5-methoxy]benzyl]-[2-(2-methoxycarbonylethyl)-5 -methoxy]benzyl]-4-methoxy-2-tert-butyldimethylsilyloxymethylhydrocinnamate

Step 18: Preparation of Methyl 5-[4-[4-[[2-(2-Methoxycarbonylethyl)-5-methoxy-4-iodo]benzyl]-[2-(2-methoxycarbonylethyl)-5-methoxy]benzyl]-[2-(2-methoxycarbonylethyl)-5-methoxy]benzyl]-4-methoxy-2-tert-butyldimethylsilyloxymethylhydrocinnamate Using essentially the procedure of Example 2, Step 6, and purifying the crude product by flash chromatography, eluting with ether/methylene chloride/hexanes (3:1:6), the desired product is prepared from methyl 5-[4-[4 -[[2-(2-methoxycarbonylethyl)-5-hydroxy-4-iodo]benzyl]-[2-(2 -methoxycarbonylethyl)-5-methoxy]benzyl]-[2-(2-methoxycarbonylethyl)-5 -methoxy]benzyl]-4-methoxy-2-tert-butyldimethylsilyloxymethylhydrocinnamate.

Step 19: Preparation of 2-(2-Methoxycarbonylethyl)-4-[4-[4-[4-[4-[[2-(2 -methoxycarbonylethyl)-5-trimethylacetyl]benzyl]-[2-(2-methoxycarbonylethyl)-5-methoxy]benzyl]-[2-(2-methoxycarbonylethyl)-5-methoxy]benzyl]-[2-(2-methoxycarbonylethyl)-5-methoxy]benzyl]-[2-(2-methoxycarbonylethyl)-5-methoxy]benzyl]-[2-(2-methoxycarbonylethyl)-5-methoxy]benzyl]-5-methoxybenzyloxy-2-tert-butyldimethylsilane Using essentially the same procedure of Example 2, Step 9, and purifying the crude product by flash chromatography, eluting with ether/methylene chloride/hexanes (2:1:2), the desired product is prepared from 5-[4-[4-[[2-(2-methoxycarbonylethyl)-5-methoxy-4-iodo]benzyl]-[2-(2 -methoxycarbonylethyl)-5-methoxy]benzyl]-[2-(2-methoxycarbonylethyl)-5 -methoxy]benzyl]-4-methoxy-2-tert-butyldimethylsilyloxymethylhydrocinnamate and methyl 5-[4-[4-[[2-(2-methoxycarbonylethyl)-5-trimethylacetyloxy]benzyl]-[2-(2-methoxycarbonylethyl)-5-methoxy]benzyl]-[2-(2-methoxycarbonylethyl)-5 -methoxy]benzyl]-4-methoxy-2-bromomethylhydrocinnamate.

A second product, 1,2-bis-[4-[4-[[2-(2-methoxycarbonylethyl)-5 -trimethylacetyloxy]benzyl]-[2-(2-methoxycarbonylethyl)-5-methoxy]benzyl]-[2 -(2-methoxycarbonylethyl)-5-methoxy]benzyl]-[2-(2-methoxycarbonylethyl)-5 -methoxy]phenyl]ethane is also isolated.

Step 20: Preparation of Methyl 5-[4-[4-[4-[4-[4-[[2-(2-Methoxycarbonylethyl)-5-trimethylacetyloxy]benzyl]-[2-(2-methoxycarbonylethyl)-5-methoxy]benzyl]-[2-(2-methoxycarbonylethyl)-5-methoxy]benzyl]-[2-(2-methoxycarbonylethyl)-5-methoxy]benzyl]-[2-(2-methoxycarbonylethyl)-5-methoxy]benzyl]-[2-(2-methoxycarbonylethyl)-5-methoxy]benzyl]-4-methoxy-2-hydroxymethylhydrocinnamate Using essentially the procedure of Example 2, Step 7, purifying the crude product by flash chromatography, eluting with ether/methylene chloride/hexanes (3:1:1) then 80% ether in methylene chloride, the desired product is prepared from 2-(2-methoxycarbonylethyl)-4-[4-[4-[4-[4-[4-[[2-(2 -methoxycarbonylethyl)-5-trimethylacetyl]benzyl]-[2-(2-methoxycarbonylethyl)-5-methoxy]benzyl]-[2-(2-methoxycarbonylethyl)-5-methoxy]benzyl]-[2-(2 -methoxycarbonylethyl)-5-methoxy]benzyl]-[2-(2-methoxycarbonylethyl)-5-methoxy]benzyl]-[2-(2-methoxycarbonylethyl)-5-methoxy]benzyl]-[2-(2 -methoxycarbonylethyl)-5-methoxy]benzyl]-5-methoxybenzyloxy-tert-butyldimethylsilane.

Step 21: Preparation of Methyl 5-[4-[4-[4-[4-[4-[[2-(2-Methoxycarbonylethyl)-5-trimethylacetyloxy]benzyl]-[2-(2-methoxycarbonylethyl)-5-methoxy]benzyl]-[2 -(2-methoxycarbonylethyl)-5-methoxy]benzyl]-[2-(2-methoxycarbonylethyl)-5-methoxy]benzyl]-[2-(2-methoxycarbonylethyl)-5-methoxy]benzyl]-[2-(2-methoxycarbonylethyl)-5-methoxy]benzyl]-[2-(2-methoxycarbonylethyl)-5-methoxy]benzyl]-4-methoxy-2-bromomethylhydrocinnamate Using essentially the procedure of Example 2, Step 8, and purifying the crude product by flash chromatography, eluting with ether, methylene chloride, hexanes (5:2:3) the desired product is prepared from 5-[4-[4-[4-[4-[4-[[2-(2 -methoxycarbonylethyl)-5-trimethylacetyloxy]benzyl]-[2-(2 -methoxycarbonylethyl)-5-methoxy]benzyl]-[2-(2-methoxycarbonylethyl)-5 -methoxy]benzyl]-[2-(2-methoxycarbonylethyl)-5-methoxy]benzyl]-[2-(2 -methoxycarbonylethyl)-5-methoxy]benzyl]-[2-(2-methoxycarbonylethyl)-5 -methoxy]benzyl]-[2-(2-methoxycarbonylethyl)-5-methoxy]benzyl]-4-methoxy-2 -hydroxymethylhydrocinnamate.

Step 22: Preparation of Methyl 5-[4-[4-[4-[4-[4-[[2-(2-Methoxycarbonylethyl)-5-hydroxy-4-iodo]benzyl]-[2-(2-methoxycarbonylethyl)-5-methoxy]benzyl]-[2-(2-methoxycarbonylethyl)-5-methoxy]benzyl]-[2-(2-methoxycarbonylethyl)-5-methoxy]benzyl]-[2-(2-methoxycarbonylethyl)-5-methoxy]benzyl]-[2-(2-methoxycarbonylethyl)-5-methoxy]benzyl]-4-methoxy-2-tert-butyldimethylsilyloxymethylhydrocinnamate Using essentially the procedure of Example 2, Step 5, and purifying the crude product by flash chromatography, eluting with ether/methylene chloride/hexanes (6:1:3), the desired product is prepared from 2-(2 -methoxycarbonylethyl)-4-[4-[4-[4-[4-[4-[[2-(2 -methoxycarbonylethyl)-5 -trimethylacetyl]benzyl]-[2-(2-methoxycarbonylethyl)-5-methoxy]benzyl]-[2-(2 -methoxycarbonylethyl)-5-methoxy]benzyl]-[2-(2-methoxycarbonylethyl)-5 -methoxy]benzyl]-[2-(2-methoxycarbonylethyl)-5-methoxy]benzyl]-[2-(2 -methoxycarbonylethyl)-5-methoxy]benzyl]-[2-(2-methoxycarbonylethyl)-5 -methoxy]benzyl]-5-methoxybenzyloxy-tert-butyldimethylsilane.

Step 23: Preparation of Methyl 5-[4-[4-[4-[4-[4-[[2-(2-Methoxycarbonylethyl)-5-methoxy-4-iodo]benzyl]-[2-(2-methoxycarbonylethyl)-5-methoxy]benzyl]-[2-(2-methoxycarbonylethyl)-5-methoxy]benzyl]-[2-(2-methoxycarbonylethyl)-5-methoxy]benzyl]-[2-(2-methoxycarbonylethyl)-5-methoxy]benzyl]-[2-(2-methoxycarbonylethyl)-5-methoxy]benzyl]-4-methoxy-2-tert-butyldimethylsilyloxymethylhydrocinnamate Using essentially the procedure of Example 2, Step 6, and purifying the crude product by flash chromatography, eluting with ether/methylene chloride/hexanes (5:2:3), the desired product is prepared from methyl 5-[4-[4 -[4-[4-[4-[4-[[2-(2-methoxycarbonylethyl)-5-hydroxy-4-iodo]benzyl] -[2 -(2-methoxycarbonylethyl)- 5-methoxy]benzyl]-[2-(2-methoxycarbonylethyl)-5 -methoxy]benzyl]-[2-(2-methoxycarbonylethyl)-5-methoxy]benzyl]-[2-(2 -methoxycarbonylethyl)-5-methoxy]benzyl]-[2-(2-methoxycarbonylethyl)-5 -methoxy]benzyl]-[2-(2-methoxycarbonylethyl)-5-methoxy]benzyl]-4-methoxy-2 -tert-butyldimethylsilyloxymethylhydrocinnamate.

Step 24: Preparation of Methyl 5-[4-[4-[4-[4-[4-[4-[4-[4-[4-[4-[4-[4-[4-[[2-(2-Methoxycarbonylethyl)-5-trimethylacetyloxy]benzyl]-[2-(2-methoxycarbonylethyl)-5-methoxy]benzyl]-[2-(2-methoxycarbonylethyl)-5-methoxy]benzyl]-[2-(2-methoxycarbonylethyl)-5-methoxy]benzyl]-[2-(2-methoxycarbonylethyl)-5-methoxy]benzyl]-[2-(2-methoxycarbonylethyl)-5-methoxy]benzyl]-[2-(2-methoxycarbonylethyl)-5-methoxy]benzyl]-[2-(2-methoxycarbonylethyl)-5-methoxy]benzyl]-[2-(2-methoxycarbonylethyl)-5-methoxy]benzyl]-[2-(2-methoxycarbonylethyl)-5-methoxy]benzyl]-[2-(2-methoxycarbonylethyl)-5-methoxy]benzyl]-[2-(2-methoxycarbonylethyl)-5-methoxy]benzyl]-4-methoxy-2-tert-butyldimethylsilyloxymethylhydrocinnamate Using essentially the procedure of Example 2, Step 9, and purifying the crude product by flash chromatography, eluting with ethyl acetate/methylene chloride/hexanes (3:2:5), and further purifying the product so obtained by flash chromatography, eluting with ethyl acetate/methylene chloride/hexanes (3:3:4), the desired product is obtained from methyl 5-[4-[4-[4-[4-[4-[4-[[2-(2 -methoxycarbonylethyl)-5-methoxy-4-iodo]benzyl]-[2-(2-methoxycarbonylethyl)-5-methoxy]benzyl]-[2-(2-methoxycarbonylethyl)-5-methoxy] benzyl]-[2-(2 -methoxycarbonylethyl)-5-methoxy]benzyl]-[2-(2-methoxycarbonylethyl)-5 -methoxy]benzyl]-[2-(2-methoxycarbonylethyl)-5-methoxy]benzyl]-[2-(2 -methoxycarbonylethyl)-5-methoxy]benzyl]-4-methoxy-2-tert-butyldimethylsilyloxymethylhydrocinnamate and methyl 5-[4-[4-[4-[4-[4-[[2 -(2-methoxycarbonylethyl)-5-trimethylacetyloxy]benzyl]-[2-(2 -methoxycarbonylethyl)-5-methoxy]benzyl]-[2-(2-methoxycarbonylethyl)-5 -methoxy]benzyl]-[2-(2-methoxycarbonylethyl)-5-methoxy]benzyl]-[2-(2 -methoxycarbonylethyl)-5-methoxy]benzyl]-[2-(2-methoxycarbonylethyl)-5 -methoxy]benzyl]-[2-(2-methoxycarbonylethyl)-5-methoxy]benzyl]-4-methoxy-2-bromomethylhydrocinnamate.

A second product, 1,2-bis-[4-[4-[4-[4-[4-[4-[4-[[2-(2-methoxycarbonylethyl)-5-trimethylacetyloxy]benzyl]-[2-(2 -methoxycarbonylethyl)-5-methoxy]benzyl]-[2-(2-methoxycarbonylethyl)-5 -methoxy]benzyl]-[2-(2-methoxycarbonylethyl)-5-methoxy]benzyl]-[2-(2 -methoxycarbonylethyl)-5-methoxy]benzyl]-[2-(2-methoxycarbonylethyl)-5 -methoxy]benzyl]-[2-(2-methoxycarbonylethyl)-5-methoxy]benzyl]-[2-(2 -methoxycarbonylethyl)-5-methoxy]phenyl]ethane is also isolated.

Step 25: Preparation of Methyl 5-[4-[4-[4-[4-[4-[4-[4-[4-[4-[4-[4-[4-[4-[[2-(2-Methoxycarbonylethyl)-5-trimethylacetyloxy]benzyl]-[2-(2 -methoxycarbonylethyl)-5-methoxy]benzyl]-[2- (2-methoxycarbonylethyl)-5-methoxy]benzyl]-[2-(2-methoxycarbonylethyl)-5-methoxy]benzyl]-[2-(2-methoxycarbonylethyl)-5-methoxy]benzyl]-[2-(2-methoxycarbonylethyl)-5-methoxy]benzyl]-[2-(2-methoxycarbonylethyl)-5-methoxy]benzyl]-[2-(2-methoxycarbonylethyl)-5-methoxy]benzyl]-[2-(2-methoxycarbonylethyl)-5-methoxy]benzyl]-[2-(2-methoxycarbonylethyl)-5-methoxy]benzyl]-[2-(2-methoxycarbonylethyl)-5-methoxy]benzyl]-[2-(2-methoxycarbonylethyl)-5-methoxy]benzyl]-4-methoxy-2-methylhydrocinnamate To a solution of the silylether product from Example 2, Step 24 (0.253 g) and acetic acid (1 ml) in THF (4 ml) is added palladium hydroxide (0.15 g) and the resulting suspension stirred under an atmosphere of hydrogen at 40° C. for about 48 hours. The hydrogen atmosphere is replaced by nitrogen and the mixture diluted with methylene chloride. The catalyst is removed by filtration and the filtrate concentrated in vacuo to give the desired product.

Step 26: Preparation of 5-[4-[4-[4-[4-[4-[4-[4-[4-[4-[4-[4-[4-[[2-(2-Carboxyethyl)-5-hydroxy]benzyl]-[2-(2-carboxyethyl)-5-hydroxy]benzyl]-[2-(2-carboxyethyl)-5-hydroxy]benzyl]-[2-(2-carboxyethyl)-5-hydroxy]benzyl]-[2-(2-carboxyethyl)-5-hydroxy]benzyl]-[2-(2-carboxyethyl)-5-hydroxy]benzyl]-[2-(2-carboxyethyl)-5-hydroxy]benzyl]-[2-(2-carboxyethyl)-5-hydroxy]benzyl]-[2-(2-carboxyethyl)-5-hydroxy]benzyl]-[2-(2-carboxyethyl)-5-hydroxy]benzyl]-[2-(2-carboxyethyl)-5-hydroxy]benzyl]-[2-(2-carboxyethyl)-5-hydroxy]benzyl]-4-hydroxy-2-methylhydrocinnamic Acid To a solution of the product from Example 2, Step 25 (0.236 g) in methylene chloride (0.5 ml) is added 1M boron tribromide in methylene chloride (4 ml). The solution is stirred at room temperature for about 60 hours, methanol (1 ml) is added dropwise, and the resulting solution poured into 10% methanol in ethyl acetate (50 ml). The solution is washed with water, brine, dried over magnesium sulfate, filtered, and concentrated in vacuo. Toluene is azeotroped from the residue and this residue is taken up in THF (1 ml) and methanol (1 ml). To this solution is added 30% aqueous sodium hydroxide (1 ml) and the solution stirred at room temperature for about 48 hours. The mixture is adjusted to pH 1 with 2N HCl, then extracted with 10% methanol in ethyl acetate. The organic layer is washed with brine, dried over magnesium sulfate, concentrated in vacuo, and the residue dissolved in concentrated aqueous ammonia solu-

EXAMPLE 3

Preparation of
1,2-Bis-[2-(2-carboxyethyl)-4-[2-(2-carboxyethyl)-5-hydroxybenzyl]-5-hydroxyphenyl]ethane Using essentially the procedure of Example 2, Step 26, the desired product is prepared from 1,2-bis-[2-(2-methoxycarbonylethyl)-4-[2-(2 -methoxycarbonylethyl)-5-trimethylacetyloxybenzyl]-5-methoxyphenyl]ethane, and isolated as the ammonium salt, m.p. 211°–214° C.

EXAMPLE 4

Preparation of
5-[4-[4-[4-[4-[4-[[2-(2-Carboxyethyl)-5-hydroxy]benzyl]-[2-(2-carboxyethyl)-5-hydroxy]benzyl]-[2-(2-carboxyethyl)-5-hydroxy]benzyl]-[2-(2-carboxyethyl)-5-hydroxy]benzyl]-[2-(2-carboxyethyl)-5-hydroxy]benzyl]-[2-(2-carboxyethyl)-5-hydroxy]benzyl]-4--hydroxy-2-methylhydrocinnamic Acid Using essentially the procedures of Example 2, Steps 25 and 26, the desired product is prepared from 2-(2-methoxycarbonylethyl)-4-[4-[4-[4-[4 -4-[[2-(2-methoxycarbonylethyl)-5-trimethylacetyl]benzyl]-[2-(2 -methoxycarbonylethyl)-5-methoxy]benzyl]-[2-(2-methoxycarbonylethyl)-5-methoxy]benzyl]-[2-(2-methoxycarbonylethyl)-5-methoxy]benzyl]-[2-(2-methoxycarbonylethyl)-5 -methoxy]benzyl]-[2-(2-methoxycarbonylethyl)-5-methoxy]benzyl]-5-methoxybenzyloxy-tert-butyldimethylsilane, and isolated as the ammonium salt.

EXAMPLE 5

Preparation of
5-[4-[4-[4-[4-[4-[[2-(2-Carboxyethyl)-5-hydroxy]benzyl[-[2-(2-carboxyethyl)-5-methoxy]benzyl]-[2-(2-carboxyethyl)-5-methoxy]benzyl]-[2-(2-carboxyethyl)-5-methoxy]benzyl]-[2-(2-carboxyethyl)-5-methoxy]benzyl]-[2-(2-carboxyethyl)-5-methoxy]benzyl]-4-methoxy-2-methylhydrocinnamic Acid Step 1: Preparation of 5-[4-[4-[4-[4-[4-[[2-(2-Carboxyethyl)-5-trimethylacetyloxy]benzyl]-[2-(2-carboxyethyl)-5-methoxy]benzyl]-[2-(2-carboxyethyl)-5-methoxy]benzyl]-[2-(2-carboxyethyl)-5-methoxy]benzyl]-[2-(2-carboxyethyl)-5-methoxy]benzyl]-[2-(2-carboxyethyl)-5-methoxy]benzyl]-4-methoxy-2-methylhydrocinnamic Acid Using essentially the procedure of Example 2, Step 25, the desired product is prepared from 2-(2-methoxycarbonylethyl)-4-[4-[4-[4-[4-[4-[[2-(2 -methoxycarbonylethyl)-5-trimethylacetyl]benzyl]-[2-(2-methoxycarbonylethyl)-5-methoxy]benzyl]-[2-(2-methoxycarbonylethyl)-5-methoxy]benzyl]-[2-(2 -methoxycarbonylethyl)-5-methoxy]benzyl]-[2-(2-methoxycarbonylethyl)-5 -methoxy]benzyl]-[2-(2-methoxycarbonylethyl)-5-methoxy]benzyl]-5-methoxybenzyloxy-tert-butyldimethylsilane.

Step 2: Preparation of 5-[4-[4-[4-[4-[4-[[2-(2-Carboxyethyl)-5-hydroxy]benzyl]-[2-(2-carboxyethyl)-5-methoxy]benzyl]-[2-(2-carboxyethyl)-5-methoxy]benzyl]-[2-(2-carboxyethyl)-5-methoxy]benzyl]-[2-(2-carboxyethyl)-5-methoxy]benzyl]-[2-(2-carboxyethyl)-5-methoxy]benzyl]-4-methoxy-2-methylhydrocinnamic Acid To a solution of the product from Example 5, Step 1 (0.18 g) in THF (1 ml) and methanol (1 ml) is added 30% aqueous sodium hydroxide (1 ml) and the resulting is stirred at room temperature for about 40 hours. The mixture is adjusted to pH 1 with 2N HCl and the solid collected by centrifugation, then washed repeatedly with water until the pH is >5.5. The solid is then dissolved in 30% aqueous ammonia and concentrated in vacuo at about 45° C. to give the desired product as the ammonium salt.

EXAMPLE 6

Preparation of
1,2-Bis-[4-[4-[4-[[2-(2-carboxyethyl)-5-hydroxy]benzyl]-[2 -(2-carboxyethyl)-5-hydroxy]benzyl]-[2-(2-carboxyethyl)-5-hydroxy]benzyl]-[2-(2-carboxyethyl)-5-hydroxy]phenyl]ethane Using essentially the procedure of Example 2, Step 26, the desired product is prepared from 1,2-bis-[4-[4-[4-[[2-(2-methoxycarbonylethyl)-5 -trimethylacetyloxy]benzyl]-[2-(2-methoxycarbonylethyl)-5-methoxy]benzyl]-[2 -(2-methoxycarbonylethyl)-5-methoxy]benzyl]-[2-(2-methoxycarbonylethyl)-5 -methoxy]phenyl]ethane.

EXAMPLE 7

Preparation of
1,2-Bis-[4-[4-[4-[[2-(2-carboxyethyl)-5-hydroxy]benzyl]-[2 -(2-carboxyethyl)-5-methoxy]benzyl]-[2-(2-carboxyethyl)-5-methoxy]benzyl]-[2-(2-carboxyethyl)-5-methoxy]phenyl]ethane Using essentially the procedure of Example 5, Step 2, the desired product is prepared, as the ammonium salt, from 1,2-bis-[4-[4-[4-[[2-(2-methoxycarbonylethyl)-5 -trimethylacetyloxy]benzyl]-[2-(2-methoxycarbonylethyl)-5-methoxy]benzyl]-[2 -(2-methoxycarbonylethyl)-5-methoxy]benzyl]-[2-(2-methoxycarbonylethyl)-5 -methoxy]phenyl]ethane.

EXAMPLE 8

Preparation of 5-[4-[4-[4-[4-[4-[4-[4-[4-[4-[4-[4-[4-[[2-(2-Carboxyethyl)-5-hydroxy]benzyl]-[2-(2-carboxyethyl)-5-methoxy]benzyl]-[2-(2-carboxyethyl)-5-methoxy]benzyl]-[2-(2-carboxyethyl)-5-methoxy]benzyl]-[2-(2-carboxyethyl)-5-methoxy]benzyl]-[2-(2-carboxyethyl)-5-methoxy]benzyl]-[2-(2-carboxyethyl)-5-methoxy]benzyl]-[2-(2-carboxyethyl)-5-methoxy]benzyl]-[2-(2-carboxyethyl)-5-methoxy]benzyl]-[2-(2-carboxyethyl)-5-methoxy]benzyl]-[2-(2-carboxy ethyl)-5-methoxy]benzyl]-[2-(2-carboxyethyl)-5-methoxy]benzyl]-4-hydroxy-2-methylhydrocinnamic Acid Using essentially the procedure of Example 5, Step 2, the desired product is prepared, and isolated as the ammonium salt, from the ester product of Example 2, Step 25.

EXAMPLE 9

Preparation of 1,2-Bis-[4-[4-[4-[4-[4-[4-[4-[[2-(2-carboxyethyl)-5-hydroxy]benzyl]-[2-(2-carboxyethyl)-5-methoxy]benzyl]-[2-(2-carboxyethyl)-5-methoxy]benzyl]-[2-(2-carboxyethyl)-5-methoxy]benzyl]-[2-(2-carboxyethyl)-5-methoxy]benzyl]-[2-(2-carboxyethyl)-5-methoxy]benzyl]-[2-(2-carboxyethyl)-5-methoxy]phenyl]ethane Using essentially the procedure of Example 5, Step 2, the desired product is prepared, and isolated as the ammonium salt, from 1,2-bis-[4-[4-[4-[4-[4-[4-[4-[[2-(2-methoxycarbonylethyl)-5-trimethylacetyloxy]benzyl]-[2-(2 -methoxycarbonylethyl)-5-methoxy]benzyl]-[2-(2-methoxycarbonylethyl)-5 -methoxy]benzyl]-[2-(2-methoxycarbonylethyl)-5-methoxy]benzyl]-[2-(2 -methoxycarbonylethyl)-5-methoxy]benzyl]-[2-(2-methoxycarbonylethyl)-5 -methoxy]benzyl]-[2-(2-methoxycarbonylethyl)-5-methoxy]benzyl]-[2-(2 -methoxycarbonylethyl)-5-methoxy]phenyl]ethane.

EXAMPLE 10

The following abbreviation is used in this example:
MMPM represents [5-(2-methoxycarbonylethyl)-2-methoxy]phenoxymethyl]

Preparation of Methyl-S-acetoxy-2-[4-[4-[4-[4-[4-[4-[4-[4-[4-[4-[4-[4-[[5-(2-methoxycarbonylethyl)-4-hydroxymethyl-2-methoxy]phenoxymethyl]-MMPM-MMPM-MMPM-MMPM-MMPM-MMPM-MMPM-MMPM-MMPM-MMPM-MMPM-MMPM-MMPM-MMPM-4-methoxyhydrocinnamate

Step 1: Preparation of 4-Acetoxy-3-methoxybenzaldehyde

A solution of vanillin (60.8 g), triethylamine (60 ml), acetic anhydride (44 ml), and 4-dimethylaminopyridine (1.0 g) in methylene chloride (800 ml) is stirred at room temperature for about 30 minues, and the volume then reduced by 50% in vacuo. The residue is diluted with ether and the solution washed with water, brine, dried over magnesium sulfate, filtered and concentrated in vacuo to give the desired product.

Step 2: Preparation of 4-Acetoxy-6-bromo-3-methoxybenzaldehyde

To a mixture of 4-acetoxy-3-methoxybenzaldehyde (75.7 g), anhydrous sodium acetate (76 g) and iodine (0.8 g) in acetic acid (300 ml) is added bromine (21 ml). The mixture is warmed to 45° C. for about 1 hour, then stirred stirred at room temperature for 3 days, poured into water (700 ml) and filtered. The solid is dissolved in toluene and the solution washed with brine, dried over magnesium sulfate, filtered and concentrated in vacuo. The residue is recrystallized twice from hexanes to give the desired product.

Step 3: Preparation of Methyl 5-Acetoxy-2-formyl-4-methoxycinnamate

To a degassed solution of 4-acetoxy-6-bromo-3-methoxybenzaldehyde (15.4 g), and bis(triphenylphosphine)palladium (11) (1.2 g) in DMF (150 ml) is added triethylamine (31.9 ml) and methyl acrylate (19.6 g). The mixture is heated 135° C. for about 1.5 hours, cooled to room temperature and diluted with ether and water. The organic layer is washed with water, brine, dried over magnesium sulfate, filtered and concentrated in vacuo. The residue is purified by HPLC, eluting with 33% ethyl acetate in hexanes, then methylene chloride, to give the desired product.

Step 4: Preparation of Methyl 5-Acetoxy-2-formyl-4-methoxyhydrocinnamate

A mixture of methyl 5-acetoxy-2-formyl-4-methoxycinnamate (10.8 g) and 10% palladium on carbon (3 g) in ethyl acetate (100 ml) is hydrogenated at 45 psi for about 18 hours and filtered. The filtrate is concentrated in vacuo and the residue purified by HPLC, eluting 50% ethyl acetate in hexanes, to give the desired product.

Step 5: Preparation of Methyl 5-Acetoxy-2-tert-butyldimethylsilyloxymethyl-4 -methoxyhydrocinnamate To a solution of methyl 5-acetoxy-2-formyl-4-methoxyhydrocinnamate (3.31 g) and imidazole (2.42 g) in methylene chloride (25 ml) is added a solution of tert-butylchlorodimethylsilane (2.73 g) in methylene chloride (25 ml). The mixture is stirred at room temperature for about 60 minutes, diluted with ether and water, and the organic layer washed with water, brine, dried over magnesium sulfate, filtered and concentrated in vacuo to give the desired product.

Step 6: Preparation of Methyl 5-Hydroxy-2-tert-butyldimethylsilyloxymethyl-4 -methoxyhydrocinnamate A mixture of methyl 5-acetoxy-2-tert-butyldimethylsilyloxymethyl-4 -methoxyhydrocinnamate (4.64 g) and potassium carbonate (0.16 g) in anhydrous methanol (50 ml) is stirred at 0°–5° C. for about 18 hours, diluted with water, and the pH adjusted to 5 with dilute HCl. The mixture is extracted with ether and the ether solution is washed with brine, dried over magnesium sulfate, filtered and concentrated in vacuo. The residue is purified by HPLC, eluting with 20% ethyl acetate in hexanes to give the desired product.

Step 7: Preparation of Methyl 5-Acetoxy-2-bromomethyl-4-methoxyhydrocinnamate To a solution of methyl 5-hydroxy-2-tert-butyldimethylsilyloxymethyl-4-methoxyhydrocinnamate (5.21 g) in carbon tetrabromide (12.35 g) in anhydrous ether (75 ml) and anhydrous THF (50 ml) is added portionwise triphenylphosphine (9.78 g) and the mixture stirred at room temperature for 60 minutes, diluted with ether, then filtered. The filtrate is concentrated in vacuo and the residue purified by filtration through silica gel in 50% ethyl acetate in hexanes followed by HPLC, eluting with 25% ethyl acetate in hexanes, to give the desired product.

Step 8: Preparation of Methyl 5-Acetoxy-2-[4-tert-butyldimethylsilyloxymethyl-2-methoxy-5-(2-methoxycarbonylethyl)]phenoxymethyl-4-methoxyhydrocinnamate To a suspension of pentane-washed sodium hydride (60% in mineral oil, 0.575 g) in anhydrous DMF (5 ml) is added dropwise a solution of methyl 5-hydroxy-2-tert-butyldimethylsilyloxymethyl-4-methoxyhydrocinnamate (4.84 g) in DMF (20 ml). The solution is stirred at room temperature for 15 minutes and a solution of methyl 5-acetoxy-2-bromomethyl-4-methoxyhydrocinnamate (5.20 g) in DMF (25 ml) is added. After stirring at room temperature for 45 minutes the mixtured is quenched with water and ether. The organic layer is washed with water, brine, dried over magnesium sulfate, filtered and concentrated in vacuo. The residue is purified by HPLC, eluting with 25% ethyl acetate in hexanes, to give the desired product.

Step 9: Preparation of Methyl 5-Acetoxy-2-[4-hydroxymethyl-2-methoxy-5-(2-methoxycarbonylethyl)]phenoxymethyl-4-methoxyhydrocinnamate To a solution of methyl 5-acetoxy-2-[4-tert-butyldimethylsilyloxymethyl-2-methoxy-5-(2-methoxycarbonylethyl)]phenoxymethyl-4-methoxyhydrocinnamate (2.51 g) and acetic acid (0.70 ml) in anhydrous THF (20 ml) is added tetrabutylammonium fluoride (6.1 ml of a 1N solution in THF). The solution is stirred at room temperature for about 60 minutes, diluted with ether and the organic solution washed with water, brine, dried over magnesium sulfate, filtered and concentrated in vacuo. The residue is purified by HPLC, eluting with 40% hexanes in ethyl acetate.

Step 10: Preparation of Methyl 5-Acetoxy-2-[4-bromomethyl-2-methoxy-5-(2-methoxycarbonylethyl)]phenoxymethyl-4-methoxyhydrocinnamate Using essentially the procedure of Example 10, Step 7, and purifying the crude product by flash chromatography, eluting with 33% ethyl acetate in hexanes, the desired is prepared from methyl 5-acetoxy-2-[4-hydroxymethyl-2-methoxy-5-(2-methoxycarbonylethyl)]phenoxymethyl-4-methoxyhydrocinnamate.

Step 11: Preparation of Methyl 5-Hydroxy-2-[4-tert-butyldimethylsilyloxymethyl-2-methoxy-5-(2-methoxycarbonylethyl)]phenoxymethyl-4-methoxyhydrocinnamate A solution of methyl 5-acetoxy-2-[4-tert-butyldimethylsilyloxymethyl-2-methoxy-5-(2-methoxycarbonylethyl)]phenoxymethyl-4-methoxyhydrocinnamate (2.57 g) and sodium methoxide (4.2 ml of a 1N solution in methanol) in THF (25 ml) is kept at −78° C. for about 18 hours, then quenched with acetic acid (0.50 ml) and diluted with ethyl acetate. The solution is washed with water, brine, dried over magnesium sulfate, filtered and concentrated in vacuo. The residue is purified by flash chromatography, eluting with 30% ethyl acetate in hexane, to give the desired product.

Step 12: Preparation of Methyl-5-acetoxy-2-[4-[4-[[5-(2-methoxycarbonylethyl)-4-tert-butyldimethylsilyloxymethyl-2-methoxy]phenoxymethyl]-MMPM-MMPM-4-methoxyhydrocinnamate A mixture of sodium hydride (0.60 g of a 60% suspension in mineral oil) in DMF (2 ml) is cooled to −15° C. and a solution of methyl 5-hydroxy-2-[4-tert-butyldimethylsilyloxymethyl-2-methoxy-5-(2-methoxycarbonylethyl)]phenoxymethyl-4-methoxyhydrocinnamate (0.803 g) in DMF (8 ml) is added. The mixture is stirred for about 30 minutes and a solution of methyl 5-acetoxy-2-[4-bromomethyl-2-methoxy-5-(2-methoxycarbonylethyl)]phenoxymethyl-4-methoxyhydrocinnamate (0.79 g) in DMF (10 ml) is added. The mixture is warmed slowly to room temperature, stirred for 2 hours, and diluted with ether and water. The aqueous layer is extracted with ether and ethyl acetate and the combined organic layers washed with water, brine, dried over magnesium sulfate, filtered and concentrated in vacuo. The residue was purified by flash chromatography, eluting with 40% ethyl acetate in hexanes, to give the desired product.

Step 13: Preparation of Methyl-5-acetoxy-2-[4-[4-[[5-(2-methoxycarbonylethyl)-4-hydroxymethyl-2-methoxy]phenoxymethyl]-MMPM-MMPM-4-methoxyhydrocinnamate Using essentially the procedure of Example 10, Step 9, the desired product, m.p. 126°–127° C., is prepared from methyl-5-acetoxy-2-[4-[4-[[5-(2-methoxycarbonylethyl)-4-tert-butyldimethylsilyloxymethyl-2-methoxy]phenoxymethyl]-MMPM-MMPM-4-methoxyhydrocinnamate.

Step 14: Preparation of Methyl-5-acetoxy-2-[4-[4-[[5-(2-methoxycarbonylethyl)-4-bromomethyl-2-methoxy]phenoxymethyl]-MMPM-MMPM-4-methoxyhydrocinnamate Using essentially the procedure of Example 10, Step 7, the desired product is prepared from methyl-5-acetoxy-2-[4-[4-[[5-(2-methoxycarbonylethyl)-4-hydroxymethyl-2-methoxy]phenoxymethyl]-MMPM-MMPM-4-methoxyhydrocinnamate.

Step 15: Preparation of Methyl-5-hydroxy-2-[4-[4-[[5-(2-methoxycarbonylethyl)-4-tert-butyldimethylsilyloxymethyl-2-methoxy]phenoxymethyl]-MMPM-MMPM-4-methoxyhydrocinnamate Using essentially the procedure of Example, Step 11, the desired product is prepared from methyl-5-acetoxy-2-[4-[4-[[5-(2-methoxycarbonylethyl)-4-tert-butyldimethylsily loxymethyl-2 -methoxy]phenoxymethyl]-MMPM-MMPM-4-methoxyhydrocinnamate.

Step 16: Preparation of
Methyl-5-acetoxy-2-[4-[4-[4-[4-[4-[4-[[5-(2-methoxycarbonylethyl)-
4-tert-butyldimethylsilyloxymethyl-2-methoxy]phenoxymethyl]-MMPM-MMPM-
MMPM-MMPM-MMPM-MMPM-4
-methoxyhydrocinnamate Using essentially the procedure of Example 10, Step 12, the desired is prepared from methyl-5-hydroxy-2-[4-[4-[[5-(2-methoxycarbonylethyl)-4 -tert-butyldimethylsilyloxymethyl- 2-methoxy]phenoxymethyl]-MMPM-MMPM-4 -methoxyhydrocinnamate and methyl-5-acetoxy-2-[4-[4-[[5-(2 -methoxycarbonylethyl)-4-bromomethyl-2-methoxy]phenoxymethyl]-MMPM-MMPM- 4-methoxyhydrocinnamate.

Step 17: Preparation of
Methyl-5-acetoxy-2-[4-[4-[4-[4-[4-[[5-(2-methoxycarbonylethyl)-
4-hydroxymethyl-2-methoxy]phenoxymethyl]-
MMPM-MMPM-MMPM-MMPM-MMPM-MMPM-
4-methoxyhydrocinnamate Using essentially the procedure of Example 10, Step 9, The desired product is prepared from methyl-5-acetoxy-2-[4-[4-[4-[4-[4-[[5-( 2-methoxycarbonylethyl)- 4-tert-butyldimethylsilyloxymethyl-2 -methoxy]phenoxymethyl]-MMPM-MMPM-MMPM-MMPM-MMPM-MMPM-4 -methoxyhydrocinnamate.

Step 18: Preparation of
Methyl-5-acetoxy-2-[4-[4-[4-[4-[4-[[5-(2-methoxycarbonylethyl)-
4-bromomethyl-2-methoxy]phenoxymethyl]-
MMPM-MMPM-MMPM-MMPM-MMPM-MMPM-
4-methoxyhydrocinnamate Using essentially the procedure of Example 10, Step 7, the desired product is prepared from methyl-5-acetoxy-2-[4-[4-[4-[4-[4-[[5-( 2-methoxycarbonylethyl)- 4-hydroxymethyl-2-methoxy]phenoxymethyl]-MMPM-MMPM-MMPM-MMPM-MMPM-4-methoxyhydrocinnamate.

Step 19: Preparation of
Methyl-5-hydroxy-2-[4-[4-[4-[4-[4-[4-[[5-(2-methoxycarbonylethyl)-
4-tert-butyldimethylsilyloxymethyl-2
-methoxy]phenoxymethyl]-MMPM-MMPM-MMPM-
MMPM-MMPM-MMPM-4-methoxyhydrocinnamate Using essentially the procedure of Example 10, Step 11, the desired product is prepared from methyl-5-acetoxy-2-[4-[4-[4-[4-[4-[[5-( 2-methoxycarbonylethyl)-4-tert-butyldimethylsilyloxymethyl-2 -methoxy]phenoxymethyl]-MMPM-MMPM-MMPM-MMPM-MMPM-MMPM-4-methoxyhydrocinnamate.

Step 20: Preparation of
Methyl-5-acetoxy-2-[4-[4-[4-[4-[4-[4-[4-[4-[4-[4-[4 -[4-[[5-(2-methoxycarbonylethyl)-4-
tert-butyldimethylsilyloxymethyl-2-
methoxy]phenoxymethyl]-MMPM-MMPM-MMPM-
MMPM-MMPM-MMPM-MMPM-MMPM-MMPM-
MMPM-MMPM-MMPM-MMPM-MMPM-
4-methoxyhydrocinnamate Using essentially the procedure of Example 10, Step 12, the desired compound is prepared from methyl-5-acetoxy-2-[4-[4-[4-[4-[4-[[5-( 2-methoxycarbonylethyl)-4-bromomethyl-2-methoxy]phenoxymethyl]-MMPM-MMPM-MMPM-MMPM-MMPM-MMPM-4-methoxyhydrocinnamate and methyl-5-acetoxy-2-[4-[4-[4-[4-[4-[[5-(2-methoxycarbonylethyl)-4 -butyldimethylsilyloxymethyl-2-methoxy]phenoxymethyl]-MMPM-MMPM-MMPM-MMPM-MMPM-MMPM-4-methoxyhydrocinnamate.

Step 21: Preparation of
Methyl-5-acetoxy-2-[4-[4-[4-[4-[4-[4-[4-
[4-[4-[4-[4-[4-
[4-[[5-(2-methoxycarbonylethyl)-4-hydroxymethyl-
2-methoxy]phenoxymethyl]-MMPM-MMPM-
MMPM-MMPM-MMPM-MMPM-MMPM-MMPM-
MMPM-MMPM-MMPM-MMPM-MMPM-MMPM-
4-methoxyhydrocinnamate Using essentially the procedure of Example 10, Step 9, the desired product is prepared from methyl-5-acetoxy-2-[4-[4-[4-[4-[4-[4-[4-[4-[4-[4-[4 -[4-[[5-(2-methoxycarbonylethyl)-4-tert-butyldimethylsilyloxymethyl-2 -methoxy]phenoxymethyl]-MMPM-MMPM-MMPM-MMPM-MMPM-MMPM-MMPM-MMPM-MMPM-MMPM-MMPM-MMPM-4-methoxyhydrocinnamate.

EXAMPLE 11

The following abbreviations are used in this example:
MMPM represents [5-(2-methoxycarbonylethyl)-2-methoxy]phenoxymethyl]
BIPM represents [2-benzyloxy-5-isobutyl]phenoxymethyl]

Preparation of
Methyl-5-acetoxy-2-[4-[4-[4-[4-[4-[4-
[4-[4-[4-[4-[4-[[5-(2-methoxycarbonylethyl)-
4-hydroxymethyl-2-methoxy]phenoxymethyl]-BIPM-
MMPM-MMPM-BIPM-MMPM-MMPM-BIPM-
MMPM-MMPM-BIPM-MMPM-MMPM-BIPM-
4-methoxyhydrocinnamate

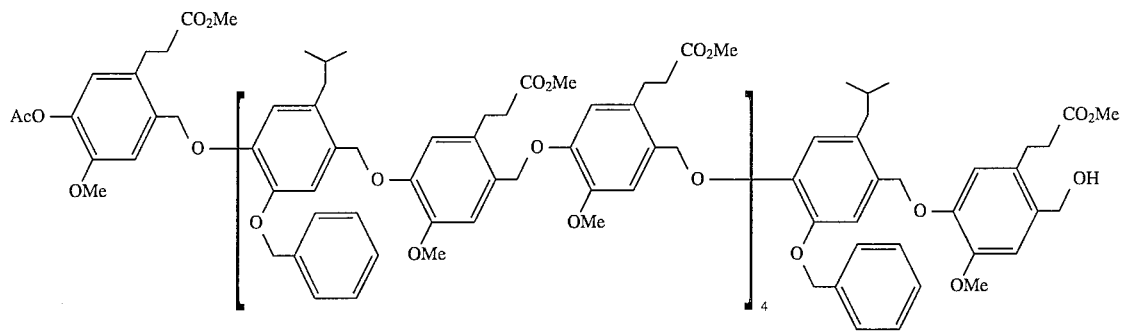

Step 1: Preparation of Methyl-5-acetoxy-2-[4-[[4-tert-butyldimethylsilyloxymethyl-5-(2-methoxycarbonylethyl)-2-methoxy]phenoxymethyl]-BIPM-4-methoxyhydrocinnamate Using essentially the procedure of Example 10, Step 8, the desired product is prepared from methyl 5-acetoxy-2-bromomethyl-4 -methoxyhydrocinnamate and methyl 5-[(5-benzyloxy-2-isobutyl-4 -hydroxy)benzyloxy]-2-tert-butyldimethylsiloxymethyl-4 -methoxyhydrocinnamate.

Step 2: Preparation of Methyl-5-acetoxy-2-[4-[[4-bromomethyl-5-(2-methoxycarbonylethyl)-2-methoxy]phenoxymethyl]-BIPM-4-methoxyhydrocinnamate Using essentially the procedures of Example 10, Steps 9 and 10, the desired product is prepared from methyl-5-acetoxy-2-[4-[[4-tert-butyldimethylsilyloxymethyl- 5-(2-methoxycarbonylethyl)-2-methoxy]phenoxymethyl]-BIPM-4-methoxyhydrocinnamate.

Step 3: Preparation of Methyl-5-hydroxy-2-[4-[[4-tert-butyldimethylsilyloxymethyl-5-(2-methoxycarbonylethyl)-2-methoxy]phenoxymethyl]-BIPM-4-methoxyhydrocinnamate Using essentially the procedure of Example 10, Step 11, the desired product is prepared from methyl-5-acetoxy-2-[4-[[4-tert-butyldimethylsilyloxymethyl- 5-(2-methoxycarbonylethyl)-2-methoxy]phenoxymethyl]-BIPM-4-methoxyhydrocinnamate.

Step 4: Preparation of Methyl-5-acetoxy-2-[4-[4-[4-[[4-tert-butyldimethylsilyloxymethyl-5-(2-methoxycarbonylethyl)-2-methoxy]phenoxymethyl]-BIPM-MMPM-MMPM-BIPM-4-methoxyhydrocinnamate Using essentially the procedure of Example 10, Step 12, the desired product is prepared from methyl-5-acetoxy-2-[4-[[4-bromomethyl-5-(2 -methoxycarbonylethyl)-2-methoxy]phenoxymethyl]-BIPM-4 -methoxyhydrocinnamate and methyl-5-hydroxy-2-[4-[[4-tert-butyldimethylsilyloxymethyl- 5-(2-methoxycarbonylethyl)-2-methoxy]phenoxymethyl]-BIPM-4-methoxyhydrocinnamate.

Step 5: Preparation of Methyl-5-acetoxy-2-[4-[4-[4-[4-[4-[4-[4-[4-[[4-tert-butyldimethylsilyloxymethyl-5-(2-methoxycarbonylethyl)-2-methoxy]phenoxymethyl]-BIPM-MMPM-MMPM-BIPM-MMPM-MMPM-BIPM-MMPM-MMPM-BIPM-4-methoxyhydrocinnamate Using essentially the procedures of Example 11, Steps 2, 3, 4, and 5, the desired product is prepared from methyl-5-acetoxy-2-[4-[4-[4-[[4 -tert-butyldimethylsilyloxymethyl-5-(2-methoxycarbonylethyl)-2 -methoxy]phenoxymethyl]-BIPM-MMPM-MMPM-BIPM-4-methoxyhydrocinnamate.

Step 6: Preparation of Methyl-5-hydroxy-2-[4-[4-[4-[4-[4-[4-[4-[4-[4-[[4-tert-butyldimethylsilyloxymethyl-5-(2-methoxycarbonylethyl)-2-methoxy]phenoxymethyl]-BIPM-MMPM-MMPM-BIPM-MMPM-MMPM-BIPM-MMPM-MMPM-BIPM-4-methoxyhydrocinnamate Using essentially the procedure of Example 10, Step 11, the desired product is prepared from methyl-5-acetoxy-2-[4-[4-[4-[4-[4-[4 -[4-[4-[4-[[4-tert-butyldimethylsilyloxymethyl- 5-(2-methoxycarbonylethyl)-2-methoxy]phenoxymethyl]-BIPM-MMPM-MMPM-BIPM-MMPM-MMPM-BIPM-MMPM-MMPM-BIPM-4-methoxyhydrocinnamate.

Step 6: Preparation of Methyl-5-acetoxy-2-[4-[4-[4-[4-[4-[4-[4-[4-[4-[4-[4-[4-[[5-(2-methoxycarbonylethyl)-4-tert-butyldimethylsilyloxymethyl-2 -methoxy]phenoxymethyl]-BIPM-MMPM-MMPM-BIPM-MMPM-MMPM-BIPM-MMPM-MMPM-BIPM-MMPM-MMPM-BIPM-4-methoxyhydrocinnamate Using essentially the procedure of Example 10, Step 12, the desired product is prepared from methyl-5-hydroxy-2-[4-[4-[4-[4-[4-[4-[4-[4-[4-[[4 -tert-butyldimethylsilyloxymethyl-5-(2-methoxycarbonylethyl)-2 -methoxy]phenoxymethyl]-BIPM-MMPM-MMPM-BIPM-MMPM-MMPM-BIPM-MMPM-MMPM-BIPM-4-methoxyhydrocinnamate and methyl-5-acetoxy-2-[4 -[[4-bromomethyl-5-(2-methoxycarbonylethyl)-2-methoxy]phenoxymethyl]-BIPM-4-methoxyhydrocinnamate.

Step 7: Preparation of Methyl-5-acetoxy-2-[4-[4-[4-[4-[4-[4-[4-[4-[4-[4-[4-[[5-(2-methoxycarbonylethyl)-4-hydroxymethyl-2-methoxy]phenoxymethyl]-BIPM-MMPM-MMPM-BIPM-MMPM-MMPM-BIPM-MMPM-MMPM-BIPM-MMPM-MMPM-BIPM-4-methoxyhydrocinnamate Using essentially the procedure of Example 10, Step 9, the desired product is prepared from methyl-5-acetoxy-2-[4-[4-[4-[4-[4-[4 -[4-[4-[4-[4-[4 -[[5-(2-methoxycarbonylethyl)-4-tert-butyldimethylsilyloxymethyl-2 -methoxy]phenoxymethyl]-BIPM-MMPM-MMPM-BIPM-MMPM-MMPM-BIPM-MMPM-MMPM-BIPM-MMPM-MMPM-BIPM- 4-methoxyhydrocinnamate.

EXAMPLE 12

Preparation of
2-[4-[4-[4-[[5-(2-Carboxyethyl)-2-methoxy]
phenoxymethyl]-[5-(2-
carboxyethyl)-2-methoxy]phenoxymethyl]-[5-
(2-carboxyethyl)-2-
methoxy]phenoxymethyl]-[5-(2-carboxyethyl)-
2-methoxy]phenoxymethyl]-4-
methoxyhydrocinnamic Acid Step 1: Preparation of
2-Bromo-5-methoxybenzaldehyde To a solution of m-anisaldehyde (25.2 g) and anhydrous sodium acetate (37.6 g) in acetic acid (150 ml) is added bromine (30.8 g) and the resulting solution stirred 45° C. overnight, then at room temperature for about 4 hours. The reaction mixture is poured into water (300 ml), stirred for 15 minutes, then filtered and the solid residue dissolved in toluene. The toluene solution is washed with brine, dried over magnesium sulfate, filtered and concentrated in vacuo. The residue is recrystallized from hexanes to give the desired product.

Step 2: Preparation of Methyl
2-Formyl-4-methoxycinnamate

Using essentially the procedure of Example 10, Step 3, and purifying the crude product by recrystallization from hexanes, the desired product is prepared from 2-bromo-5-methoxybenzaldehyde.

Step 3: Preparation of Methyl
2-Hydroxymethyl-4-methoxyhydrocinnamate

A mixture of methyl 2-formyl-4-methoxycinnamate (15.9 g) and 10% palladium on carbon (2.0 g) in ethyl acetate (200 ml) is shaken under a hydrogen pressure of 45 psi for about 18 hours. The mixture is filtered, concentrated in vacuo, and the residue purified by HPLC, eluting with hexanes/ethyl acetate (3:2), to give the desired product.

Step 4: Preparation of Methyl
2-bromomethyl-4-methoxyhydrocinnamate

Using essentially the procedure of Example 10, Step 7, and purifying the crude product by HPLC, eluting with 10% ethyl acetate in hexanes, the desired product is prepared from methyl 2-hydroxymethyl-4-methoxyhydrocinnamate.

Step 5: Preparation of Methyl-2-[4-[[5-(2-
methoxycarbonylethyl)-4-tert-
butyldimethylsilyloxymethyl-
2-methoxy]phenoxymethyl]-[5-
(2-methoxycarbonylethyl)-
2-methoxy]phenoxymethyl]-4-methoxyhydrocinnamate Using essentially the procedure of Example 10, Step 8, and purifying the crude product by flash chromatography, eluting with hexanes/ethyl acetate (2:1), the desired product is prepared from methyl 5-hydroxy-2-[4-tert-butyldimethylsilyloxymethyl- 2-methoxy-5-(2-methoxycarbonylethyl)]phenoxymethyl-4-methoxyhydrocinnamate and methyl 2-bromomethyl-4-methoxyhydrocinnamate.

Step 6: Preparation of
Methyl-2-[4-[[5-(2-methoxycarbonylethyl)-4-
hydroxymethyl-2-methoxy]phenoxymethyl]-[5-
(2-methoxycarbonylethyl)-2-
methoxy]phenoxymethyl]-4-methoxyhydrocinnamate Using essentially the procedure of Example 10, Step 9, the desired product is prepared from methyl-2-[4-[[5-(2-methoxycarbonylethyl)-4 -tert-butyldimethylsilyloxymethyl-2-methoxy]phenoxymethyl]-[5-(2 -methoxycarbonylethyl)-2-methoxy]phenoxymethyl]-4-methoxyhydrocinnamate.

Step 7: Preparation of
Methyl-2-bromomethyl-4-methoxy-5-[2-(2-
methoxycarbonylethyl)-5-methoxybenzyloxy]
hydrocinnamate To a solution of methyl-2-[4-[[5-(2-methoxycarbonylethyl)-4 -hydroxymethyl-2-methoxy]phenoxymethyl]-[5-(2-methoxycarbonylethyl)-2 -methoxy]phenoxymethyl]-4-methoxyhydrocinnamate (0.282 g) in chloroform (5 ml) is added dropwise bromotrimethylsilane (0.167 ml) and the solution stirred at room temperature for 5 minutes, then diluted with ethyl acetate and saturated sodium bicarbonate solution. The organic layer is washed with water, brine, dried over magnesium sulfate, filtered and concentrated in vacuo. The residue is purified by flash chromatography, eluting with hexanes/ethyl acetate (3:1) to give the desired product.

Step 8: Preparation of
Methyl-5-acetoxy-2-[4-[[5-(2-methoxycarbonylethyl)-
2-methoxy]phenoxymethyl]-[5-(2-
methoxycarbonylethyl)-2-
methoxy]phenoxymethyl]-4-methoxyhydrocinnamate Using essentially the procedure of Example 10, Step 8, and purifying the crude product by flash chromatography, eluting with hexanes/ethyl acetate (1:1), the desired product is prepared from methyl 5-acetoxy-2-[4-bromomethyl-2-methoxy-5-(2-methoxycarbonylethyl)]phenoxymethyl-4 -methoxyhydrocinnamate and methyl-3-hydroxy-4-methoxyhydroxycinnamate.

Step 9: Preparation of
Methyl-5-hydroxy-2-[4-[[5-(2-
methoxycarbonylethyl)-2-
methoxy]phenoxymethyl]-[5-
(2-methoxycarbonylethyl)-2-
methoxy]phenoxymethyl]-4-methoxyhydrocinnamate A solution of methyl-5-acetoxy-2-[4-[[5-(2-methoxycarbonylethyl)-2 -methoxy]phenoxymethyl]-[5-(2-methoxycarbonylethyl)-2 -methoxy]phenoxymethyl]-4-methoxyhydrocinnamate (0.197 g) in THF (3 ml) is cooled to −78° C., and a 1M solution of sodium methoxide in methanol (0.34 ml) is added dropwise. The resulting solution is stirred at −78° C. for about 20 hours, then quenched with acetic acid (0.20 ml), and diluted with water and ethyl acetate. The organic layer is washed with water, brine, dried over magnesium sulfate, filtered and concentrated in vacuo to give the desired product.

Step 10: Preparation of Methyl
2-[4-[4-[4-[[5-(2-methoxycarbonylethyl)-2-
methoxy]phenoxymethyl]-[5-
(2-methoxycarbonylethyl)-2-
methoxy]phenoxymethyl]-[5-
(2-methoxycarbonylethyl)-2-
methoxy]phenoxymethyl]-[5-
(2-methoxycarbonylethyl)-2-
methoxy]phenoxymethyl]-4-methoxyhydrocinnamate Using essentially the procedure of Example 10, Step 8, and purifying the crude by flash chromatography, eluting with hexanes/ethyl acetate (3:2), the desired product is prepared from methyl-5-hydroxy-2-[4-[[5-(2 -methoxycarbonylethyl)-2-methoxy]phenoxymethyl]-[5-(2 -methoxycarbonylethyl)-2-methoxy]phenoxymethyl]-4-methoxyhydrocinnamate and methyl-2-bromomethyl-4-methoxy-5-[2-(2-methoxycarbonylethyl)-5 -methoxybenzyloxy] hydrocinnamate.

Step 11: Preparation of
2-[4-[4-[4-[[5-(2-Carboxyethyl)-2-
methoxy]phenoxymethyl]-[5-(2-carboxyethyl)-
2-methoxy]phenoxymethyl]-[5-(2-
carboxyethyl)-2-methoxy]phenoxymethyl]-
[5-(2-carboxyethyl)-2-
methoxy]phenoxymethyl]-4-methoxyhydrocinnamic
Acid To a solution of methyl 2-[4-[4-[4-[[5-(2-methoxycarbonylethyl)-2 -methoxy]phenoxymethyl]-[5-(2-methoxycarbonylethyl)-2 -methoxy]phenoxymethyl]-[5-(2-methoxycarbonylethyl)-2 -methoxy]phenoxymethyl]-[5-(2-methoxycarbonylethyl)-2 -methoxy]phenoxymethyl]-4-methoxyhydrocinnamate (0.145 g) in methanol (1.5 ml) is added 1N sodium hydroxide solution (1.5 ml). The mixture is stirred at room temperature for about 2 hours and THF (2 ml) is added. This mixture is stirred at room temperature for about 18 hours and concentrated in vacuo to about one-half volume. This mixture is cooled to 0° C. and the pH adjusted to 4 with 10% HCl, then filtered. The solid residue is washed with water, dried, and dissolved in 10% aqueous ammonia and this solution concentrated in vacuo to give the desired product as the ammonium salt, m.p. 199°–201° C.

EXAMPLE 13

Preparation of Polymer of
3,4-Dihydroxy-6-methylphenylacetic Acid and
Formaldehyde A solution of 3,4-dihydroxy-6-methylphenylacetic acid (1.72 g) and s-trioxane (0.25 g) in acetic acid (5 ml) is heated to 90° C. and acetic acid/concentrated sulfuric acid (4:1) (0.25 ml) is added. The mixture is heated at 90° C. for four hours, then poured into ice water. The mixture is filtered, the solid washed with water, then dissolved in dilute aqueous ammonia. The solution is concentrated in vacuo at 40°–45° C. to give the desired product as the ammonium salt.

Various of the above oligomers have been tested for their biological activity in processes normally associated with glycosaminoglycan-protein interaction. In these tests, the activity of the compounds tested indicates their ability to bind with bioactive proteins, as described earlier herein. It is believed that the results of the tests presented below correlate to biological activities of the tested compounds in human and animal patients.

Inhibition of Heparinase Activity

Heparinase is an endoglucuronidase capable of degrading heparin sulfate (HS) at specific intrachain sites. Studies on degradation of sulfated proteoglycans in the subendothelial extracellular matrix (ECM) demonstrate a correlation between heparinase activity and the metastatic potential of various tumor cells. Heparanase activity is also suggested to play a role in the mobilization of normal circulating cells of the immune system during inflammatory processes.

The ability of compounds of the present invention to inhibit lymphoma-cell derived heparinase is tested in the assay system described by Vlodavsky et al., *Cancer Research* 43, 2704–2711 (1983). $^{35}$S labeled ECM is incubated for 24 hours with ESb mouse lymphoma heparinase in the presence of various concentrations of the polymers tested. Degradation of the HS is followed by gel filtration of the supernatants. Heparanase activity is expressed as the total amount of labeled low-molecular-weight fragments released from the EMC substrate.

Induction of Lipoprotein Lipase Release In-Vivo

The enzyme lipoprotein lipase (LPL) participates in the process of lipid transfer from the bloodstream to the tissues. LPL is bound to the external surface of endothelial cells via non-covalent association with cell-membrane glycosaminoglycans. Therefore, the injection of heparin results in a rapid release of LPL into the bloodstream.

In order to test for heparin-like activity, male albino rats (about 200 g) are injected with 10 mg/kg body weight of the oligomers tested in saline. Blood samples are taken from the animals immediately before the injection (time O) and 30 minutes afterwards. LPL activity is measured on duplicates of serum aliquot.

The assay system consists of 0.1 ml of serum sample and 0.1 ml of substrate containing labeled triolein, prepared according to the method of Nilsson-Ehle and Schotz, *J. Lipid Res.* 17, 536–541 (1976). Incubations are carried out at 37° C. for 45 minutes. The reaction is stopped by the addition of methanol/chloroform/heptane (1.4:1.25:1 v/v) and the extraction of fatty acids is performed according to the method of Belfrage et al, *J. Lipid Res.* 10, 341–344 (1969), as modified by Nilsson-Ehle and Schotz. Enzyme activity is calculated according to the formula of Nilsson-Ehle and Schotz.

Oligomeric compounds exhibiting activity in the foregoing tests may be useful in the treatment of cardiovascular diseases such as artherosclerosis.

Anticoagulation Activity

The following test measures anticoagulant activity of the oligomers of the present invention and utilizes the Activated Partial Thromboplastin Time (APTT) test, with the following procedures.

To an assay cuvette is added 100 µl of normal pooled plasma (George King Biomedical Inc., Kansas) and 100 ml of a solution containing the test compound in aqueous 50 mM Tris hydrochloride at pH 7.5 (0.2 mg of sample in one ml buffer). The sample is placed in a MLA coagulation timer which automatically maintains the sample at 37° C. for 2.5 minutes, 100 µl of actin activated cephaloplastin reagent is injected, kept 5 minutes, 100 µl of 35 mM CaCl is injected, and clot formation is determined photometrically and the clotting time recorded. Each example is examined at a variety of concentrations, generally from about 0.025 mg/ml bonylethyl)-4-tert-butyldimethylsilyloxymethyl-2 -methoxy]phenoxymethyl]-BIPM-MMPM-MMPM-BIPM-MMPM-MMPM-BIPM-MMPM-MMPM-BIPM-MMPM-MMPM-BIPM- 4-methoxyhydrocinnamate.

EXAMPLE 12

Preparation of
2-[4-[4-[4-[[5-(2-Carboxyethyl)-2-methoxy]
phenoxymethyl]-[5-(2-
carboxyethyl)-2-methoxy]phenoxymethyl]-[5-
(2-carboxyethyl)-2-
methoxy]phenoxymethyl]-[5-(2-carboxyethyl)-
2-methoxy]phenoxymethyl]-4-
methoxyhydrocinnamic Acid Step 1: Preparation of
2-Bromo-5-methoxybenzaldehyde To a solution of m-anisaldehyde (25.2 g) and anhydrous sodium acetate (37.6 g) in acetic acid (150 ml) is added bromine (30.8 g) and the resulting solution stirred 45° C. overnight, then at room temperature for about 4 hours. The reaction mixture is poured into water (300 ml), stirred for 15 minutes, then filtered and the solid residue dissolved in toluene. The toluene solution is washed with brine, dried over magnesium sulfate, filtered and concentrated in vacuo. The residue is recrystallized from hexanes to give the desired product.

Step 2: Preparation of Methyl
2-Formyl-4-methoxycinnamate

Using essentially the procedure of Example 10, Step 3, and purifying the crude product by recrystallization from hexanes, the desired product is prepared from 2-bromo-5-methoxybenzaldehyde.

Step 3: Preparation of Methyl
2-Hydroxymethyl-4-methoxyhydrocinnamate

A mixture of methyl 2-formyl-4-methoxycinnamate (15.9 g) and 10% palladium on carbon (2.0 g) in ethyl acetate (200 ml) is shaken under a hydrogen pressure of 45 psi for about 18 hours. The mixture is filtered, concentrated in vacuo, and the residue purified by HPLC, eluting with hexanes/ethyl acetate (3:2), to give the desired product.

Step 4: Preparation of Methyl
2-bromomethyl-4-methoxyhydrocinnamate

Using essentially the procedure of Example 10, Step 7, and purifying the crude product by HPLC, eluting with 10% ethyl acetate in hexanes, the desired product is prepared from methyl 2-hydroxymethyl-4-methoxyhydrocinnamate.

Step 5: Preparation of Methyl-2-[4-[[5-(2-
methoxycarbonylethyl)-4-tert-
butyldimethylsilyloxymethyl-
2-methoxy]phenoxymethyl]-[5-
(2-methoxycarbonylethyl)-
2-methoxy]phenoxymethyl]-4-methoxyhydrocinnamate Using essentially the procedure of Example 10, Step 8, and purifying the crude product by flash chromatography, eluting with hexanes/ethyl acetate (2:1), the desired product is prepared from methyl 5-hydroxy-2-[4-tert-butyldimethylsilyloxymethyl- 2-methoxy-5-(2-methoxycarbonylethyl)]phenoxymethyl-4-methoxyhydrocinnamate and methyl 2-bromomethyl-4-methoxyhydrocinnamate.

Step 6: Preparation of
Methyl-2-[4-[[5-(2-methoxycarbonylethyl)-4-
hydroxymethyl-2-methoxy]phenoxymethyl]-[5-
(2-methoxycarbonylethyl)-2-
methoxy]phenoxymethyl]-4-methoxyhydrocinnamate Using essentially the procedure of Example 10, Step 9, the desired product is prepared from methyl-2-[4-[[5-(2-methoxycarbonylethyl)-4 -tert-butyldimethylsilyloxymethyl-2-methoxy]phenoxymethyl]-[5-(2 -methoxycarbonylethyl)-2-methoxy]phenoxymethyl]-4-methoxyhydrocinnamate.

Step 7: Preparation of
Methyl-2-bromomethyl-4-methoxy-5-[2-(2-
methoxycarbonylethyl)-5-methoxybenzyloxy]
hydrocinnamate To a solution of methyl-2-[4-[[5-(2-methoxycarbonylethyl)-4 -hydroxymethyl-2-methoxy]phenoxymethyl]-[5-(2-methoxycarbonylethyl)-2 -methoxy]phenoxymethyl]-4-methoxyhydrocinnamate (0.282 g) in chloroform (5 ml) is added dropwise bromotrimethylsilane (0.167 ml) and the solution stirred at room temperature for 5 minutes, then diluted with ethyl acetate and saturated sodium bicarbonate solution. The organic layer is washed with water, brine, dried over magnesium sulfate, filtered and concentrated in vacuo. The residue is purified by flash chromatography, eluting with hexanes/ethyl acetate (3:1) to give the desired product.

Step 8: Preparation of
Methyl-5-acetoxy-2-[4-[[5-(2-methoxycarbonylethyl)-
2-methoxy]phenoxymethyl]-[5-(2-
methoxycarbonylethyl)-2-
methoxy]phenoxymethyl]-4-methoxyhydrocinnamate Using essentially the procedure of Example 10, Step 8, and purifying the crude product by flash chromatography, eluting with hexanes/ethyl acetate (1:1), the desired product is prepared from methyl 5-acetoxy-2-[4-bromomethyl-2-methoxy-5-(2-methoxycarbonylethyl)]phenoxymethyl-4 -methoxyhydrocinnamate and methyl-3-hydroxy-4-methoxyhydroxycinnamate.

Step 9: Preparation of
Methyl-5-hydroxy-2-[4-[[5-(2-
methoxycarbonylethyl)-2-
methoxy]phenoxymethyl]-[5-
(2-methoxycarbonylethyl)-2-
methoxy]phenoxymethyl]-4-methoxyhydrocinnamate A solution of methyl-5-acetoxy-2-[4-[[5-(2-methoxycarbonylethyl)-2 -methoxy]phenoxymethyl]-[5-(2-methoxycarbonylethyl)-2 -methoxy]phenoxymethyl]-4-methoxyhydrocinnamate (0.197 g) in THF (3 ml) is cooled to −78° C., and a 1M solution of sodium methoxide in methanol (0.34 ml) is added dropwise. The resulting solution is stirred at −78° C. for about 20 hours, then quenched with acetic acid (0.20 ml), and diluted with water and ethyl acetate. The organic layer is washed with water, brine, dried over magnesium sulfate, filtered and concentrated in vacuo to give the desired product.

Step 10: Preparation of Methyl 2-[4-[4-[4-[[5-(2-methoxycarbonylethyl)-2-methoxy]phenoxymethyl]-[5-(2-methoxycarbonylethyl)-2-methoxy]phenoxymethyl]-[5-(2-methoxycarbonylethyl)-2-methoxy]phenoxymethyl]-[5-(2-methoxycarbonylethyl)-2-methoxy]phenoxymethyl]-4-methoxyhydrocinnamate Using essentially the procedure of Example 10, Step 8, and purifying the crude by flash chromatography, eluting with hexanes/ethyl acetate (3:2), the desired product is prepared from methyl-5-hydroxy-2-[4-[[5-(2 -methoxycarbonylethyl)-2-methoxy]phenoxymethyl]-[5-(2 -methoxycarbonylethyl)-2-methoxy]phenoxymethyl]-4-methoxyhydrocinnamate and methyl-2-bromomethyl-4-methoxy-5-[2-(2-methoxycarbonylethyl)-5 -methoxybenzyloxy] hydrocinnamate.

Step 11: Preparation of 2-[4-[4-[4-[[5-(2-Carboxyethyl)-2-methoxy]phenoxymethyl]-[5-(2-carboxyethyl)-2-methoxy]phenoxymethyl]-[5-(2-carboxyethyl)-2-methoxy]phenoxymethyl]-[5-(2-carboxyethyl)-2-methoxy]phenoxymethyl]-4-methoxyhydrocinnamic Acid To a solution of methyl 2-[4-[4-[4-[[5-(2-methoxycarbonylethyl)-2 -methoxy]phenoxymethyl]-[5-(2-methoxycarbonylethyl)-2 -methoxy]phenoxymethyl]-[5-(2-methoxycarbonylethyl)-2 -methoxy]phenoxymethyl]-[5-(2-methoxycarbonylethyl)-2 -methoxy]phenoxymethyl]-4-methoxyhydrocinnamate (0.145 g) in methanol (1.5 ml) is added 1N sodium hydroxide solution (1.5 ml). The mixture is stirred at room temperature for about 2 hours and THF (2 ml) is added. This mixture is stirred at room temperature for about 18 hours and concentrated in vacuo to about one-half volume. This mixture is cooled to 0° C. and the pH adjusted to 4 with 10% HCl, then filtered. The solid residue is washed with water, dried, and dissolved in 10% aqueous ammonia and this solution concentrated in vacuo to give the desired product as the ammonium salt, m.p. 199°–201° C.

EXAMPLE 13

Preparation of Polymer of 3,4-Dihydroxy-6-methylphenylacetic Acid and Formaldehyde A solution of 3,4-dihydroxy-6-methylphenylacetic acid (1.72 g) and s-trioxane (0.25 g) in acetic acid (5 ml) is heated to 90° C. and acetic acid/concentrated sulfuric acid (4:1) (0.25 ml) is added. The mixture is heated at 90° C. for four hours, then poured into ice water. The mixture is filtered, the solid washed with water, then dissolved in dilute aqueous ammonia. The solution is concentrated in vacuo at 40°–45° C. to give the desired product as the ammonium salt.

Various of the above oligomers have been tested for their biological activity in processes normally associated with glycosaminoglycan-protein interaction. In these tests, the activity of the compounds tested indicates their ability to bind with bioactive proteins, as described earlier herein. It is believed that the results of the tests presented below correlate to biological activities of the tested compounds in human and animal patients.

Inhibition of Heparinase Activity

Heparinase is an endoglucuronidase capable of degrading heparin sulfate (HS) at specific intrachain sites. Studies on degradation of sulfated proteoglycans in the subendothelial extracellular matrix (ECM) demonstrate a correlation between heparinase activity and the metastatic potential of various tumor cells. Heparanase activity is also suggested to play a role in the mobilization of normal circulating cells of the immune system during inflammatory processes.

The ability of compounds of the present invention to inhibit lymphoma-cell derived heparinase is tested in the assay system described by Vlodavsky et al., *Cancer Research* 43, 2704–2711 (1983). $^{35}S$ labeled ECM is incubated for 24 hours with ESb mouse lymphoma heparinase in the presence of various concentrations of the polymers tested. Degradation of the HS is followed by gel filtration of the supernatants. Heparanase activity is expressed as the total amount of labeled low-molecular-weight fragments released from the EMC substrate.

Induction of Lipoprotein Lipase Release In-Vivo

The enzyme lipoprotein lipase (LPL) participates in the process of lipid transfer from the bloodstream to the tissues. LPL is bound to the external surface of endothelial cells via non-covalent association with cell-membrane glycosaminoglycans. Therefore, the injection of heparin results in a rapid release of LPL into the bloodstream.

In order to test for heparin-like activity, male albino rats (about 200 g) are injected with 10 mg/kg body weight of the oligomers tested in saline. Blood samples are taken from the animals immediately before the injection (time O) and 30 minutes afterwards. LPL activity is measured on duplicates of serum aliquot.

The assay system consists of 0.1 ml of serum sample and 0.1 ml of substrate containing labeled triolein, prepared according to the method of Nilsson-Ehle and Schotz, *J. Lipid Res.* 17, 536–541 (1976). Incubations are carried out at 37° C. for 45 minutes. The reaction is stopped by the addition of methanol/chloroform/heptane (1.4:1.25:1 v/v) and the extraction of fatty acids is performed according to the method of Belfrage et al, *J. Lipid Res.* 10, 341–344 (1969), as modified by Nilsson-Ehle and Schotz. Enzyme activity is calculated according to the formula of Nilsson-Ehle and Schotz.

Oligomeric compounds exhibiting activity in the foregoing tests may be useful in the treatment of cardiovascular diseases such as artherosclerosis.

Anticoagulation Activity

The following test measures anticoagulant activity of the oligomers of the present invention and utilizes the Activated Partial Thromboplastin Time (APTT) test, with the following procedures.

To an assay cuvette is added 100 µl of normal pooled plasma (George King Biomedical Inc., Kansas) and 100 ml of a solution containing the test compound in aqueous 50 mM Tris hydrochloride at pH 7.5 (0.2 mg of sample in one ml buffer). The sample is placed in a MLA coagulation timer which automatically maintains the sample at 37° C. for 2.5 minutes, 100 µl of actin activated cephaloplastin reagent is injected, kept 5 minutes, 100 µl of 35 mM CaCl is injected, and clot formation is determined photometrically and the clotting time recorded. Each example is examined at a variety of concentrations, generally from about 0.025 mg/ml to about 1 mg/ml, and the clotting times are graphed as a function of concentration. From the graphic results, the concentration required to double clotting time ($IC_{DCT}$) is calculated by linear interpolation.

Inhibition of Ristocetin and Botrocetin-Induced Binding of vWF Platelets

The binding of vWf (vonWillebrand Factor) to glycoprotein Ib is measured in one of two experimental systems, in the presence of either ristocetin or botrocetin as modulators of binding. The ristocetin modulated binding is described herein.

Formalin-fixed platelets, prepared according to the method of MacFarlane, D. et al., *Thromb. Diath. Haemorrh.* 34, 306–308 (1975), were pre-incubated at room temperature for 15 minutes with specified dilutions of oligomers according to the present invention. Ristocetin, (Sigma, St. Louis, Mo.) diluted to a final concentration of 1.0 mg/ml, and $^{125}$I-labelled multimeric vWF (isolated from human plasma cryoprecipitate according to the method of Fulcher, C. A. et al. *Proc. Natl. Acad. Sci. USA*, 79, 1648–1652 (1982), and labelled according to the method of Fraker, P. J. et al. *Biochem. Biophys. Res. Commun.*, 80, 849–857 (1978)) were then added to the incubation mixture, and the amount of $^{125}$I-vWF bound to the platelets was determined. 125I-vWF binding to the platelets was referenced against 100% binding which was defined as the amount of 125I-vWF bound in the absence of added oligomer compound. The method for measuring vWF binding is reported in detail in Ruggeri et al., *J. Clin. Invest.*, 72, 1–12, (1983), herein incorporated by reference.

Platelet Aggregation Inhibition

The method for measuring platelet aggregation inhibition is essentially that of Ruggeri, et al., *Proc. Natl. Acad. Sci. USA*, 83, 5708–5712 (1986), using formalin-fixed platelets as prepared by Plow, et al., *Proc. Natl. Acad. Sci. USA*, 79, 3711–3715 (1982). A given amount of the compound of the present invention or other compound to be tested (10 to 100 µl of a 1 mg/ml solution) is incubated at 37° C. with 400 µl of human fixed thrombin activated platelets for 2 minutes. 12.5 µl of human fibrinogen solution is added and aggregation is monitored using a platelet aggregation profiler (Model PAP-4). Controls consist of fibrinogen added to incubated platelets and the resulting aggregation is considered as 100%. Percent inhibition in the presence of a given concentration of test compound versus concentration of the compound is plotted and the concentration required to give 50% inhibition ($IC_{50}$) is determined.

Compounds within the scope of the present invention have been determined to exhibit a marked activity in the foregoing tests, the results of which are presented in Table I below. The oligomeric compounds are identified in Table I by (1) their example number disclosed hereinabove, and (2) in brackets, the number of units making up the oligomer followed by the number of free carboxylic acids in each oligomer molecule.

TABLE I

Results of Anticoagulant and Antithrombotic Assays

| Compound Example No [#-mer,#-$CO_2$H] | APTT $IC_{DCT}$ (µg/ml) | Platelet Aggregation $IC_{50}$ (µg/ml) | Ristocetin-Induced Inhibition of vWF Binding to Gp1b $IC_{50}$ (µg/ml) |
|---|---|---|---|
| Ex 10, Step 13 [4,0] | >250 | | |
| Ex 1, Step 3 [4,4] | >250 | | >100 |
| Ex 12, Step 11 [5,5] | >250 | | >100 |
| Ex 3 [4,4] | 700 | | 21% at 100 µg/ml |
| Ex 7 [8,8] | 500 | | 17% at 100 µg/ml |
| Ex 6 [8,8] | 387 | >1 mg/ml | 42% at 100 µg/ml |
| Ex 4 [8,8] | 430 | >1 mg/ml | 50% at 100 µg/ml |
| Ex 5, Step 2 [8,8] | 37 | >1 mg/ml | |
| Ex 9 [16,16] | 105 | 319 | |
| Ex 2, Step 26 | 35 | 250 | |
| Ex 8 [16,16] | 35 | | |
| (Polymer 1)[1] | 15 | 0.6 | |
| (Polymer 2)[2] | 17 | 0.38 | |

[1] Compound of Example 13, co-pending case Ser. No. 07/440,587.
[2] Compound of Example 13, this case.

The foregoing results indicate that oligomers of the present invention exhibit anticoagulant and/or antithrombotic activity, and that the potency and activity thereof are related to the number of monomeric groups comprising the oligomer chain, the nature of the linking groups and the number and nature of negatively charged substituents thereon.

Human Granulocyte Elastase Inhibition Assay

The Human Granulocyte Elastase Inhibition assay is a standard test procedure and is essentially that of Kramps, et al., "L-PyroglutamyI-L-prolyl-L-valine-p-nitroanilide, a highly specific substrate for granulocyte elastase", *Scand. J. clin. Lab. Invest.* 43, 427–432 (1983).

A stock solution of 8.0 mM L-pyroglutamyI-L-prolyl-L-valine-p-nitroanilide (S-2484, obtained from Kabi) in dimethylsulfoxide is diluted to 2.0 mM in 0.03M Tris buffer, pH 8.3, to give the working substrate solution. Human neutrophil elastase (obtained from ICN Biochemical) is diluted in the same buffer to 1 unit/ml to give the working enzyme solution.

A control assay is run in which a solution of 10 µl of buffer and 10 µl of working enzyme solution is incubated at room temperature for 1 minute and 330 µl of buffer and 50 µl of working substrate solution is then added. The increase in absorbance ($\Delta OD$/min) at 405 nm is measured.

In the experimental assay 10 µl of a solution containing a compound of the present invention (in concentrations ranging from 1 mg/ml to 0.1 µg/ml), or other inhibitor to be tested, in buffer is substituted for the 10 µl of buffer with which the enzyme is incubated in the control assay and the procedure followed as for the control assay above. The $\Delta OD$/min is measured and the result expressed as percentage inhibition for the given concentration of inhibitor as compared with the $\Delta OD$/min for the control. Percent inhibition versus concentration of compound of the present invention or other inhibitor is plotted and the data extrapolated to give the concentration required for 50% inhibition of the enzyme ($IC_{50}$).

It has been unexpectedly found that compounds within the scope of the present invention have been found to markedly inhibit the activity of human nuetrophil elastase.

Table II below presents the results of the elastase inhibition assay in terms of $IC_{50}$ values of compounds within the scope of the present invention and polymers disclosed herein and/or claimed in copending Ser. No. 07/440,587.

TABLE II

Results of Human Granulocyte Elastase Inhibition Assay

| Compound of Example [#-mer,#-$CO_2H$] | $IC_{50}$ (nM) | $IC_{50}$ (ng/ml) |
|---|---|---|
| Ex 12, Step 11 [5,5] | >1000 | >1000 |
| Ex 3 [4,4] | >1000 | >1000 |
| Ex 7 [8,8] | 22 | 34 |
| Ex 6 [8,8] | 24 | 36 |
| Ex 4 [8,8] | 20 | 30 |
| Ex 2, Step 19, Second Product [8,0] | >1000 | >1000 |
| Ex 5, Step 2 [8,8] | 30 | 50 |
| (Polymer 1)[1] | | 130 |
| (Polymer 2)[2] | | 40 |

[1]Compound of Example 13, co-pending case Ser. No. 07/440,587.
[2]Compound of Example 13, this case.

Inhibition of DNA Binding to Anti-DNA Antibodies

In order to study the effect of the oligomeric compounds on nucleic acid-protein interaction, the binding of DNA to anti-DNA mouse antibodies (MoAb) is employed as a model.

The anti-DNA A52 hybridoma antibody (IgG 2b,k) was produced by fusion of a BALB/C myeloma cell line with spleen cells of unimmunized, female NZB/NZW FI mice as described previously (Eilat et al., *J. Immunol.* 133, 489–494 (1984)). The nitrocellulose filter assay for the binding of radiolabeled DNA to the specific antibody was performed essentially as described in Eilat. Briefly, reaction mixtures contained 10 µl (50 5 ng, 4000 cpm) of *E. coli* $^{14}$C DNA (Amersham, Buckinghamshire, England), 10 µl of medium containing A52 mouse hybridoma IgG, 10 µl of the tested inhibitor (in saline) and 0.1 ml of 0.2M borate buffered saline pH 8. In experiments designed to measure how successfully the compunds of the present invention compete with DNA in binding to DNA-specific antibodies, different concentrations of the compounds tested are mixed with radioactive DNA before adding the antibodies. The binding mixtures are left for 15 minutes at 37° C., followed by 1 hour at 4° C., then filtered through 0.45 µm nitrocellulose filters (Millipore, Bedford, Mass.). The filters are washed twice with borate buffered saline (3 ml), then dried and counted in a toluene-based scintillation liquid.

The foregoing pharmacological results indicate that the potency and activity of the oligomers of the present invention are related to the number and nature of the charged substituents thereon. It is believed that a component of the means by which the oligomers of the present invention exert their biological activity is electrostatic interaction at charged biological sites. Consequently, compounds of the present invention have at least one substituent which bears a positive or negative charge at biological pH, or have at least one substituent which may be converted by metabolic or other biological processes to such a charged substituent, i.e. in the manner of a prodrug.

Compounds useful in the present invention are useful in the treatment of cardiovascular disorders such as thrombosis, bone metabolic disorders, hypolipaemic disorders, neuronal disorders, gastrointestinal disorders, disorders which may be treated by agents effective in binding DNA, and elastase-mediated connective tissue degradation disorders.

The dosage regimen in carrying out the methods of this invention is that which insures maximum therapeutic response until improvement is obtained and thereafter the minimum effective level which gives relief. In general, the oral dose may be between about 3 mg/kg and about 1000 mg/kg (preferably in the range of 10 to 300 mg/kg), and the i.v. dose about 0.1 mg/kg to about 10 mg/kg (preferably in the range of about 0.5 to about 5 mg/kg), bearing in mind, of course, that in selecting the appropriate dosage in any specific case, consideration must be given to the patient's weight, general health, age and other factors which may influence response to the drug. The drug may be administered as frequently as is necessary to achieve and sustain the desired therapeutic response. Some patients may respond quickly to a relatively large or small dose and require little or no maintenance dosage. On the other hand, other patients may require sustained dosing from about 1 to about 4 times a day depending on the physiological needs of the particular patient. Usually the drug may be administered orally 1 to 4 times per day. It is anticipated that many patients will require no more than about one to about two doses daily.

Pharmaceutical compositions according to the present invention useful in the treatment of one or more of the foregoing disorders comprise one or more oligomeric compounds as described herein in an amount effective by either oral or parenteral administration to inhibit the binding of bioactive macromolecules involved in the pathology of such disorder.

Compositions of this invention may be formulated for administration in any convenient way, and the invention includes within its scope orally and parenterally administrable pharmaceutical compositions containing at least one oligomeric compound as described hereinabove adapted for use in human or veterinary medicine. Such compositions may be formulated in a conventional manner using one or more pharmaceutically acceptable carriers or excipients. Suitable carriers include diluents or fillers, sterile aqueous media and various non-toxic organic solvents. The compositions may be formulated in the form of tablets, capsules, lozenges, troches, hard candies, powders, aqueous suspensions, or solutions, injectable solutions, elixirs, syrups and the like and may contain one or more agents selected from the group including sweetening agents, flavoring agents, coloring agents and preserving agents, in order to provide a pharmaceutically acceptable preparation.

The particular carrier and the ratio of therapeutically effective compound to carrier are determined by the solubility and chemical properties of the compounds, the particular mode of administration and standard pharmaceutical practice. For example, excipients such as lactose, sodium citrate, calcium carbonate and dicalcium phosphate and various disintegratants such as starch, alginic acid and certain complex silicates, together with lubricating agents such as magnesium stearate, sodium lauryl; sodium lauryl sulphate and talc, can be used in producing tablets. For a capsule form, lactose and high molecular weight polyethylene glycols are among the preferred pharmaceutically acceptable carriers. Where aqueous suspensions for oral use are formulated, the carrier can be emulsifying or suspending agents.

Diluents such as ethanol, propylene glycol, glycerin and chloroform and their combinations can be employed as well as other materials.

For parenteral administration such as intramuscular and subcutaneous injection, solutions or suspensions of the polymeric compounds in sesame or peanut oil or aqueous propylene glycol solutions, as well as sterile aqueous solutions can be employed. The aqueous solutions using pure distilled water are also useful for intravenous injection purposes, provided that their pH is properly adjusted, suitably buffered, made isotonic with sufficient saline or glucose and sterilized by heating or by microfiltration.

It is also anticipated that the present invention would be useful as an injectable dosage form which may be administered in an emergency to a patient suffering from stroke or heart attack. Such treatment may be followed by intravenous infusion of the active oligomeric compound and the amount of compound infused into such a patient should be effective to achieve and maintain the desired therapeutic response.

It will be evident to those skilled in the art that the invention is not limited to the details of the foregoing illustrative examples and that the present invention may be embodied in other specific forms without departing from the essential attributes thereof, and it is therefore desired that the present embodiments and examples be considered in all respects as illustrative and not restrictive, reference being made to the appended claims, rather than to the foregoing description, and all changes which come within the meaning and range of equivalency of the claims are therefore intended to be embraced therein.

What is claimed is:

1. A pharmaceutical composition comprising, in admixture with a pharmaceutically acceptable carrier, a linear oligomeric compound according to the formula

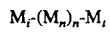

wherein:

n represents a sequence of whole numbers beginning at 3 and having an upper limit of about 50;

$M_i$ is

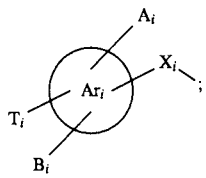

$M_n$ is

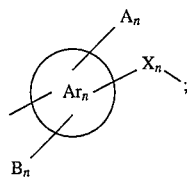

$M_t$ is

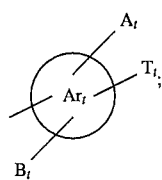

where

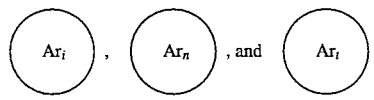

are independently aromatic carbocyclic or aromatic heterocyclic rings;

where

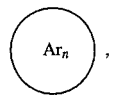

$A_n$, $B_n$, and $X_n$ may be the same or different for each of the $(M_n)_n$ groups in the n sequence; and $A_i$, $B_i$, $A_n$, $B_n$, $A_t$, and $B_t$ are independently hydrogen, alkyl, aralkyl, cyano, alkoxyalkoxy, or —$(CH_2)_a$—W—$(CH_2)_b$—$R_s$, where $R_s$ is NRR', COOR, CONRR', NR(COR'), PO(OR)$_2$, COR, SO$_2$OR, OSO$_2$OR, halogen, OR, SO$_2$R, SOR, SR, or CHO, and where a and b are independently 0 to about 4, (a+b) is less than about 5, W is —O—, —S—, —SO—, —SO$_2$—, —NR(COR')—, —NR—, or a bond, and R and R' are independently hydrogen, alkyl or aralkyl, provided that at least one of the substituent groups, $A_i$, $B_i$, $A_n$, $B_n$, $A_t$, and $B_t$, is —$(CH_2)_a$—W—$(CH_2)_b$—$R_s$ where $R_s$ is other than hydroxy or halogen;

$T_i$ and $T_t$ are independently hydrogen, alkyl, alkenyl, halo, cyano, alkoxyalkoxy, haloalkyl, hydroxy, tert-butyldimethylsilyloxyalkyl, hydroxyalkyl, alkoxy, aralkoxy, aryloxy, alkoxyalkyl, aralkoxyalkyl, aryloxyalkyl, mercapto, mercaptoalkyl, alkylthio, aralkylthio, alkylthioalkyl, aralkylthioalkyl, arylthioalkyl, amino, alkylamino, aminoalkyl, alkylaminoalkyl, acylamino, acylaminoalkyl, carboxy, carboxyalkyl, alkoxycarbonyl, alkoxycarbonylalkyl, aralkoxycarbonyl, aralkoxycarbonylalkyl, aryloxycarbonyloxy, formyl, formylalkyl, acyl, acyloxy, and acylalkyl;

$X_i$ and $X_n$ are independently —$(CR_1R_2)_m$—Y—$(CR_3R_4)_p$— where $R_1$, $R_2$, $R_3$, and $R_4$ are independently hydrogen or alkyl, m and p are independently 0 to about 5, provided that (m+p) is 0 to about 5, and Y is a bond or —O—, provided that when Y is —O—, then either m or p is 0;

provided that at least one of $A_i$, $B_i$, $A_n$, $B_n$, $A_t$, $B_t$, $T_i$ and $T_t$ is NRR', COOR, NR(COR'), PO(OR)$_2$, COR, $SO_2OR$, $OR$, $SO_2R$, $SR$, or $CHO$; and provided further that when

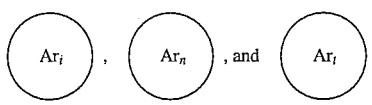

are all naphthalene, then at least one of $A_i$, $B_i$, $A_n$, $B_n$, $A_t$, and $B_t$ is $—(CH_2)_a—W—(CH_2)_b—R_s$ where $R_s$ is $COOR$;

or a pharmaceutically acceptable salt thereof.

2. A pharmaceutical composition of claim 1 wherein:

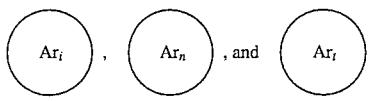

are independently benzene, naphthalene, pyridine, quinoline, or isoquinoline.

3. A pharmaceutical composition of claim 1 wherein:

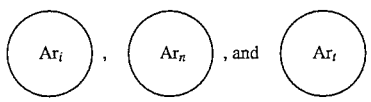

are independently benzene or naphthalene.

4. A pharmaceutical composition of claim 3 wherein n is a sequence of whole numbers having an upper limit of from about four to about 8.

5. A pharmaceutical composition of claim 1 wherein n is a sequence of whole numbers beginning at 2 and having an upper limit of 18 and wherein $(M_n)_n$ represents from two to about 18 monomeric units.

6. A pharmaceutical composition of claim 5 wherein n is a sequence of whole numbers beginning at 4 and having an upper limit of 14 and wherein $(M_n)_n$ represents from 4 to about 14 monomeric units.

7. A pharmaceutical composition of claim 6 wherein n is a sequence of whole numbers beginning at 6 and having an upper limit of about 18 and wherein $(M_n)_n$ represents from 6 to about 18 monomeric units.

8. A pharmaceutical composition of claim 1 wherein: $M_i$ is

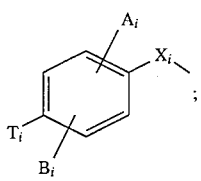

$M_n$ is

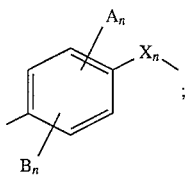

and $M_t$ is

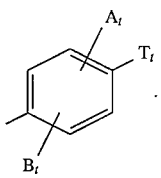

9. A pharmaceutical composition of claim 1 wherein: $M_i$ is

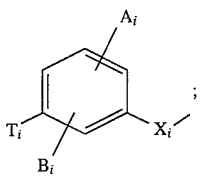

$M_n$ is

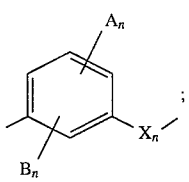

and $M_t$ is

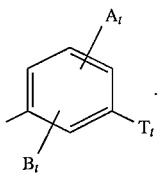

10. A pharmaceutical composition of claim 1 comprising a linear oligomeric compound of the formula

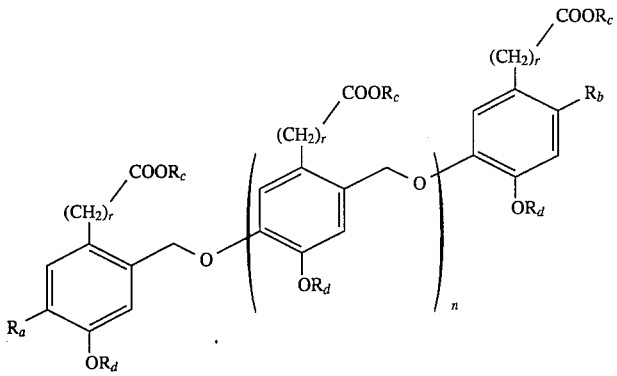

wherein:

$R_a$ is hydrogen, hydroxy, or acyloxy;

$R_b$ is hydrogen, alkyl, or hydroxyalkyl;

$R_c$ is hydrogen or alkyl;

$R_d$ is hydrogen or alkyl;

r is 1 through about 4; and n is 2 to about 30;

or a pharmaceutically acceptable salt thereof.

11. A pharmaceutical composition of claim 1 comprising a linear oligomeric compound of the formula

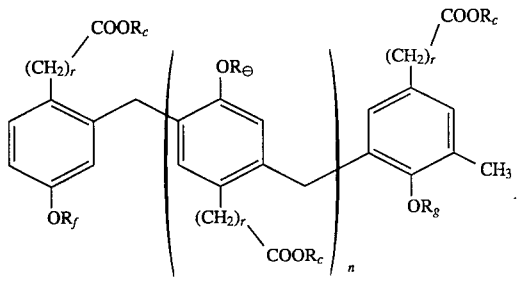

wherein:

$R_e$, $R_c$, $R_f$, and $R_g$ are independently hydrogen or alkyl;

r is 1 to about 4; and n is 1 to about 30;

or a pharmaceutically acceptable salt thereof.

12. A pharmaceutical composition of claims 8, 9, 10 or 11 wherein n is a sequence of whole numbers having an upper limit of from about four to about 8.

13. A method for the prevention of blood clotting comprising the administration to a human or other animal patient in need of anticoagulant therapy of a pharmaceutical composition of claim 12 in an effective anticoagulant amount.

14. A method for the prevention and treatment of an elastase-mediated connective tissue degradation disorder comprising the administration to a human or other animal patient in need of such therapy of a pharmaceutical composition of claim 12 in an effective elastase-inhibiting amount.

15. A pharmaceutical composition of claim 1 comprising a linear oligomeric compound which is 2-[4-[4-[4-[[5-(2-carboxyethyl)-2-methoxy]phenoxymethyl]-[5-(2-carboxyethyl)-2-methoxy]phenoxymethyl]-[5-(2-carboxyethyl)-2 -methoxy]phenoxymethyl]-[5-(2-carboxyethyl)-2-methoxy] phenoxymethyl]-4 -methoxyhydrocinnamic acid or a pharmaceutically acceptable salt thereof.

16. A pharmaceutical composition of claim 1 comprising a linear oligomeric compound which is 1,2-bis-[4-[4-[4-[[2-(2-carboxyethyl)-5-hydroxy]benzyl]-[2 -(2-carboxyethyl)-5-hydroxy]benzyl]-[2-(2-carboxyethyl)-5-hydroxy]benzyl]-[2-(2-carboxyethyl)-5-hydroxy]phenyl]ethane or a pharmaceutically acceptable salt thereof.

17. A pharmaceutical composition of claim 1 comprising a linear oligomeric compound which is bis-[5-(2-carboxyethyl)-3-[5-(2-carboxyethyl)-2 -hydroxybenzyl]-2-hydroxyphenyl]methane or a pharmaceutically acceptable salt thereof.

18. A pharmaceutical composition of claim 1 comprising a linear oligomeric compound which is methyl-5-acetoxy-2-[4-[4-[[5-(2 -methoxycarbonylethyl)-4-hydroxymethyl-2-methoxy]phenoxymethyl]-[5-(2 -methoxycarbonylethyl)-2-methoxy]phenoxymethyl]-[5-(2 -methoxycarbonylethyl)-2-methoxy]phenoxymethyl]-4-methoxyhydrocinnamate or a pharmaceutically acceptable salt thereof.

19. A pharmaceutical composition of claim 1 comprising a linear oligomeric compound which is 1,2-bis-[2-(2-carboxyethyl)-4-[2-(2-carboxyethyl)-5 -hydroxybenzyl]-5-hydroxyphenyl]ethane or a pharmaceutically acceptable salt thereof.

20. A pharmaceutical composition of claim 1 comprising a linear oligomeric compound which is 5-[4-[4-[4-[4-[4-[[2-(2-carboxyethyl)-5 -hydroxy]benzyl]-[2-(2-carboxyethyl)-5-hydroxy]benzyl]-[2-(2-carboxyethyl)-5-hydroxy] benzyl]-[2-(2 -carboxyethyl)-5-hydroxy]benzyl]-[2-(2-carboxyethyl)-5-hydroxy]benzyl]-[2-(2 -carboxyethyl)-5-hydroxy]benzyl]-[2-(2-carboxyethyl)-5-hydroxy]benzyl]-4 -hydroxy-2-methylhydrocinnamic acid or a pharmaceutically acceptable salt thereof.

21. A pharmaceutical composition of claim 1 comprising a linear oligomeric compound which is 2-(2-methoxycarbonylethyl)-4-[4-[4-[4-[4-[4-[[2-(2-methoxycarbonylethyl)-5-trimethylacetyloxy]benzyl]-[2-(2-methoxycarbonylethyl)-5-methoxy]benzyl]-[2-(2-methoxycarbonylethyl)-5-methoxy]benzyl]-[2-(2 -methoxycarbonylethyl)-5-methoxy]benzyl]-[2-(2-methoxycarbonylethyl)-5 -methoxy]benzyl]-[2-(2-methoxycarbonylethyl)-5-methoxy]benzyl]-[2-(2 -methoxycarbonylethyl)-5-methoxy]benzyl]-5-methoxybenzyloxy-tert-butyldimethylsilane or a pharmaceutically acceptable salt thereof.

22. A pharmaceutical composition of claim 1 comprising a linear oligomeric compound which is 1,2-bis-[4-[4-[4-[[2-(2-methoxycarbonylethyl)-5 -trimethylacetyloxy]benzyl]-[2-(2-methoxycarbonylethyl)-5-methoxy]benzyl]-[2-(2 -methoxycarbonylethyl)-5-methoxy]benzyl]-[2-(2-methoxycarbonylethyl)-5 -methoxy]phenyl]ethane or a pharmaceutically acceptable salt thereof.

23. A pharmaceutical composition of claim 1 comprising a linear oligomeric compound which is 5-[4-[4-[4-[4-[4-[[2-(2-carboxyethyl)-5 -hydroxy]benzyl]-[2-(2-carboxyethyl)-5-methoxy]benzyl]-[2-(2-carboxyethyl)-5-methoxy]

benzyl]-[2-(2-carboxyethyl)-5-methoxy]benzyl]-[2-(2-carboxyethyl)-5-methoxy]benzyl]-[2-(2-carboxyethyl)-5-methoxy]benzyl]-[2-(2-carboxyethyl)-5-methoxy]benzyl]-4-methoxy-2-methylhydrocinnamic acid or a pharmaceutically acceptable salt thereof.

24. A pharmaceutical composition of claim 1 comprising a linear oligomeric compound which is 5-[4-[4-[4-[4-[4-[4-[4-[4-[4-[4-[4-[4-[[2-(2-carboxyethyl)-5-hydroxy]benzyl]-[2-(2-carboxyethyl)-5-hydroxy]benzyl]-[2-(2-carboxyethyl)-5-hydroxy]benzyl]-[2-(2-carboxyethyl)-5-hydroxy]benzyl]-[2-(2-carboxyethyl)-5-hydroxy]benzyl]-[2-(2-carboxyethyl)-5-hydroxy]benzyl]-[2-(2-carboxyethyl)-5-hydroxy]benzyl]-[2-(2-carboxyethyl)-5-hydroxy]benzyl]-[2-(2-carboxyethyl)-5-hydroxy]benzyl]-[2-(2-carboxyethyl)-5-hydroxy]benzyl]-[2-(2-carboxyethyl)-5-hydroxy]benzyl]-[2-(2-carboxyethyl)-5-hydroxy]benzyl]-4-hydroxy-2-methylhydrocinnamic acid or a pharmaceutically acceptable salt thereof.

25. A pharmaceutical composition of claim 1 comprising a linear oligomeric compound which is 1,2-bis-[4-[4-[4-[4-[4-[4-[[2-(2-carboxyethyl)-5-hydroxy]benzyl]-[2-(2-carboxyethyl)-5-methoxy]benzyl]-[2-(2-carboxyethyl)-5-methoxy]benzyl]-[2-(2-carboxyethyl)-5-methoxy]benzyl]-[2-(2-carboxyethyl)-5-methoxy]benzyl]-[2-(2-carboxyethyl)-5-methoxy]benzyl]-[2-(2-carboxyethyl)-5-methoxy]benzyl]-[2-(2-carboxyethyl)-5-methoxy]phenyl]ethane or a pharmaceutically acceptable salt thereof.

26. A pharmaceutical composition of claim 1 comprising a linear oligomeric compound which is 5-[4-[4-[4-[4-[4-[4-[4-[4-[4-[4-[4-[4-[[2-(2-carboxyethyl)-5-hydroxy]benzyl]-[2-(2-carboxyethyl)-5-methoxy]benzyl]-[2-(2-carboxyethyl)-5-methoxy]benzyl]-[2-(2-carboxyethyl)-5-methoxy]benzyl]-[2-(2-carboxyethyl)-5-methoxy]benzyl]-[2-(2-carboxyethyl)-5-methoxy]benzyl]-[2-(2-carboxyethyl)-5-methoxy]benzyl]-[2-(2-carboxyethyl)-5-methoxy]benzyl]-[2-(2-carboxyethyl)-5-methoxy]benzyl]-[2-(2-carboxyethyl)-5-methoxy]benzyl]-[2-(2-carboxyethyl)-5-methoxy]benzyl]-[2-(2-carboxyethyl)-5-methoxy]benzyl]-4-hydroxy-2-methylhydrocinnamic acid or a pharmaceutically acceptable salt thereof.

27. A pharmaceutical composition of claim 1 comprising a linear oligomeric compound which is methyl-5-acetoxy-2-[4-[4-[4-[4-[4-[4-[[5-(2-methoxycarbonylethyl)-4-hydroxymethyl-2-methoxy]phenoxymethyl]-[5-(2-methoxycarbonylethyl)-2-methoxy]phenoxymethyl]-[5-(2-methoxycarbonylethyl)-2-methoxy]phenoxymethyl]-[5-(2-methoxycarbonylethyl)-2-methoxy]phenoxymethyl]-[5-(2-methoxycarbonylethyl)-2-methoxy]phenoxymethyl]-[5-(2-methoxycarbonylethyl)-2-methoxy]phenoxymethyl]-[5-(2-methoxycarbonylethyl)-2-methoxy]phenoxymethyl]-4-methoxyhydrocinnamate.

28. A pharmaceutical composition of claim 1 comprising a linear oligomeric compound which is methyl-5-acetoxy-2-[4-[4-[4-[4-[4-[4-[4-[4-[4-[4-[4-[4-[4-[[5-(2-methoxycarbonylethyl)-4-hydroxymethyl-2-methoxy]phenoxymethyl]-[5-(2-methoxycarbonylethyl)-2-methoxy]phenoxymethyl]-[5-(2-methoxycarbonylethyl)-2-methoxy]phenoxymethyl]-[5-(2-methoxycarbonylethyl)-2-methoxy]phenoxymethyl]-[5-(2-methoxycarbonylethyl)-2-methoxy]phenoxymethyl]-[5-(2-methoxycarbonylethyl)-2-methoxy]phenoxymethyl]-[5-(2-methoxycarbonylethyl)-2-methoxy]phenoxymethyl]-[5-(2-methoxycarbonylethyl)-2-methoxy]phenoxymethyl]-[5-(2-methoxycarbonylethyl)-2-methoxy]phenoxymethyl]-[5-(2-methoxycarbonylethyl)-2-methoxy]phenoxymethyl]-[5-(2-methoxycarbonylethyl)-2-methoxy]phenoxymethyl]-[5-(2-methoxycarbonylethyl)-2-methoxy]phenoxymethyl]-[5-(2-methoxycarbonylethyl)-2-methoxy]phenoxymethyl]-4-methoxyhydrocinnamate.

29. A pharmaceutical composition of claim 1 comprising a linear oligomeric compound which is 1,2-bis-[4-[4-[4-[[2-(2-carboxyethyl)-5-hydroxy]benzyl]-[2-(2-carboxyethyl)-5-methoxy]benzyl]-[2-(2-carboxyethyl)-5-methoxy]benzyl]-[2-(2-carboxyethyl)-5-methoxy]phenyl]ethane or a pharmaceutically acceptable salt thereof.

30. A method for the treatment of cardiovascular disorders, or elastase-mediated connective tissue degradation disorders comprising the administration to a human or other animal patient in need of such therapy of a pharmaceutical composition of claim 1.

31. A method for the treatment and prevention of thrombosis comprising the administration to a human or other animal patient in need of antithrombotic therapy of a pharmaceutical composition of claim 1 in an effective antithrombotic amount.

32. A linear oligomeric compound according to the formula

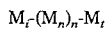

wherein:

n represents a sequence of whole numbers beginning at 3 and having an upper limit of about 50;

$M_i$ is

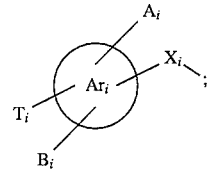

$M_n$ is

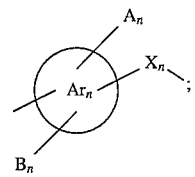

$M_t$ is

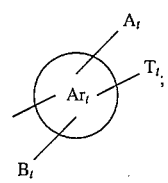

where

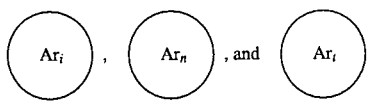

are independently aromatic carbocyclic or aromatic heterocyclic rings;

where

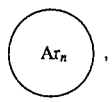

$A_n$, $B_n$, and $X_n$ may be the same or different for each of the $(M_n)_n$ groups in the n sequence; and $A_i$, $B_i$, $A_n$, $B_n$, $A_t$, and $B_t$ are independently hydrogen, alkyl, aralkyl, cyano, alkoxyalkoxy, or $-(CH_2)_a-W-(CH_2)_b-R_s$, where $R_s$ is NRR', COOR, CONRR', NR(COR'), PC(OR)$_2$, COR, SO$_2$OR, OSO$_2$OR, halogen, OR, SO$_2$R, SOR, SR, or CHO, and where a and b are independently 0 to about 4, (a+b) is less than about 5, W is $-O-$, $-S-$, $-SO-$, $-SO_2-$, $-NR(COR')-$, $-NR-$, or a bond, and R and R' are independently hydrogen, alkyl or aralkyl, provided that at least one of the substituent groups, $A_i$, $B_i$, $A_n$, $B_n$, $A_t$, and $B_t$, is $-(CH_2)_a-W-(CH_2)_b-R_s$ where $R_s$ is other than hydroxy or halogen;

$T_i$ and $T_t$ are independently hydrogen, alkyl, alkenyl, halo, cyano, alkoxyalkoxy, haloalkyl, hydroxy, tert-butyldimethylsilyloxyalkyl, hydroxyalkyl, alkoxy, aralkoxy, aryloxy, alkoxyalkyl, aralkoxyalkyl, aryloxyalkyl, mercapto, mercaptoalkyl, alkylthio, aralkylthio, alkylthioalkyl, aralkylthioalkyl, arylthioalkyl, amino, alkylamino, aminoalkyl, alkylaminoalkyl, acylamino, acylaminoalkyl, carboxy, carboxyalkyl, alkoxycarbonyl, alkoxycarbonylalkyl, aralkoxycarbonyl, aralkoxycarbonylalkyl, aryloxycarbonyloxy, formyl, formylalkyl, acyl, acyloxy, and acylalkyl;

$X_i$ and $X_n$ are independently $-(CR_1R_2)_m-Y-(CR_3R_4)_p-$ where $R_1$, $R_2$, $R_3$, and $R_4$ are independently hydrogen or alkyl, m and p are independently 0 to about 5, provided that (m+p) is 0 to about 5, and Y is a bond or $-O-$, provided that when Y is $-O-$, then either m or p is 0;

provided that at least one of $A_i$, $B_i$, $A_n$, $B_n$, $A_t$, $B_t$, $T_i$ and $T_t$ is NRR', COOR, NR(COR'), PO(OR)$_2$, COR, SO$_2$OR, OR, SO$_2$R, SR, or CHO; and provided further that when

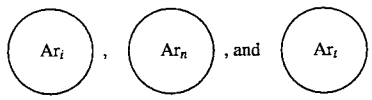

are all naphthalene, then at least one of $A_i$, $B_i$, $A_n$, $B_n$, $A_t$, and $B_t$ is $-(CH_2)_a-W-(CH_2)_b-R_s$ where Rs is COOR;

or a pharmaceutically acceptable salt thereof.

* * * * *